United States Patent
Kobayashi et al.

(10) Patent No.: US 7,323,260 B2
(45) Date of Patent: Jan. 29, 2008

(54) LUBRICANT, RECORDING MEDIUM AND CARBOXYLIC ACID COMPOUND

(75) Inventors: Ken Kobayashi, Kanagawa (JP); Tomoe Sato, Kanagawa (JP); Yutaka Iwamoto, Kanagawa (JP); Tadashi Ozue, Kanagawa (JP); Seiichi Onodera, Miyagi (JP); Takahiro Kawana, Miyagi (JP)

(73) Assignee: Sony Corporation, Tokyo (JP)

( * ) Notice: Subject to any disclaimer, the term of this patent is extended or adjusted under 35 U.S.C. 154(b) by 484 days.

(21) Appl. No.: 10/959,819

(22) Filed: Oct. 6, 2004

(65) Prior Publication Data

US 2005/0282044 A1 Dec. 22, 2005

(30) Foreign Application Priority Data

Oct. 16, 2003 (JP) ............................. 2003-356432
Aug. 23, 2004 (JP) ............................. 2004-242050

(51) Int. Cl.
G11B 5/66 (2006.01)
G11B 5/70 (2006.01)

(52) U.S. Cl. .............................. 428/835.6; 428/835.7; 428/843.4; 428/843.5

(58) Field of Classification Search ............ 428/835.6, 428/835.7, 835.8, 843.4, 843.5; 508/459, 508/496, 499; 560/190, 197
See application file for complete search history.

(56) References Cited

U.S. PATENT DOCUMENTS 3,124,533 A * 3/1964 Metro et al. ................ 508/485
4,205,085 A * 5/1980 Shepherd .................... 514/567

OTHER PUBLICATIONS

Machine translation of Furuya et al., JP 2001-055593, Japan, Feb. 2001.*
Machine translation of Darsow et al., JP 09-020704, Japan, Jan. 1997.*
Machine translation of Kai et al., JP 06-041561, Japan, Feb. 1994.*

* cited by examiner

Primary Examiner—Holly Rickman
(74) Attorney, Agent, or Firm—Robert J. Depke; Rockey, Depke & Lyons, LLC.

(57) ABSTRACT

The present invention provides a lubricant capable of holding an excellent lubricating property under various types of service conditions, maintaining a lubricating effect for a long period of time and providing excellent traveling property, abrasion resistance, durability and the like, a recording medium using the lubricant and a carboxylic acid type compound constituting the lubricant. The lubricant is formed by using a carboxylic acid type compound having at least two carboxyl groups and one ester bond as represented by the following general formula (1) (for example, a compound as represented by the following chemical formula (1)) as a constituting mixture and, then, the thus-formed lubricant is allowed to be contained on or in a recording layer of the recording medium:

(general formula 1)
$$Rf\!-\!Es\!-\!R\!-\!\underset{\underset{\displaystyle CH_2\!-\!COOH}{|}}{CH}\!-\!COOH; \text{ and}$$

(chemical formula 1)
$$CF_3(CF_2)_7(CH_2)_{10}\!-\!\underset{\underset{\displaystyle O}{\|}}{C}\!-\!O\!-\!\underset{\underset{\displaystyle CH_2\!-\!COOH}{|}}{CH}\!-\!COOH,$$

in which Rf represents a non-substituted or substituted, saturated or unsaturated, fluorine-containing hydrocarbon group or hydrocarbon group; Es represents an ester bond; and R may be omitted or represent a non-substituted or substituted, saturated or unsaturated hydrocarbon group.

10 Claims, 9 Drawing Sheets

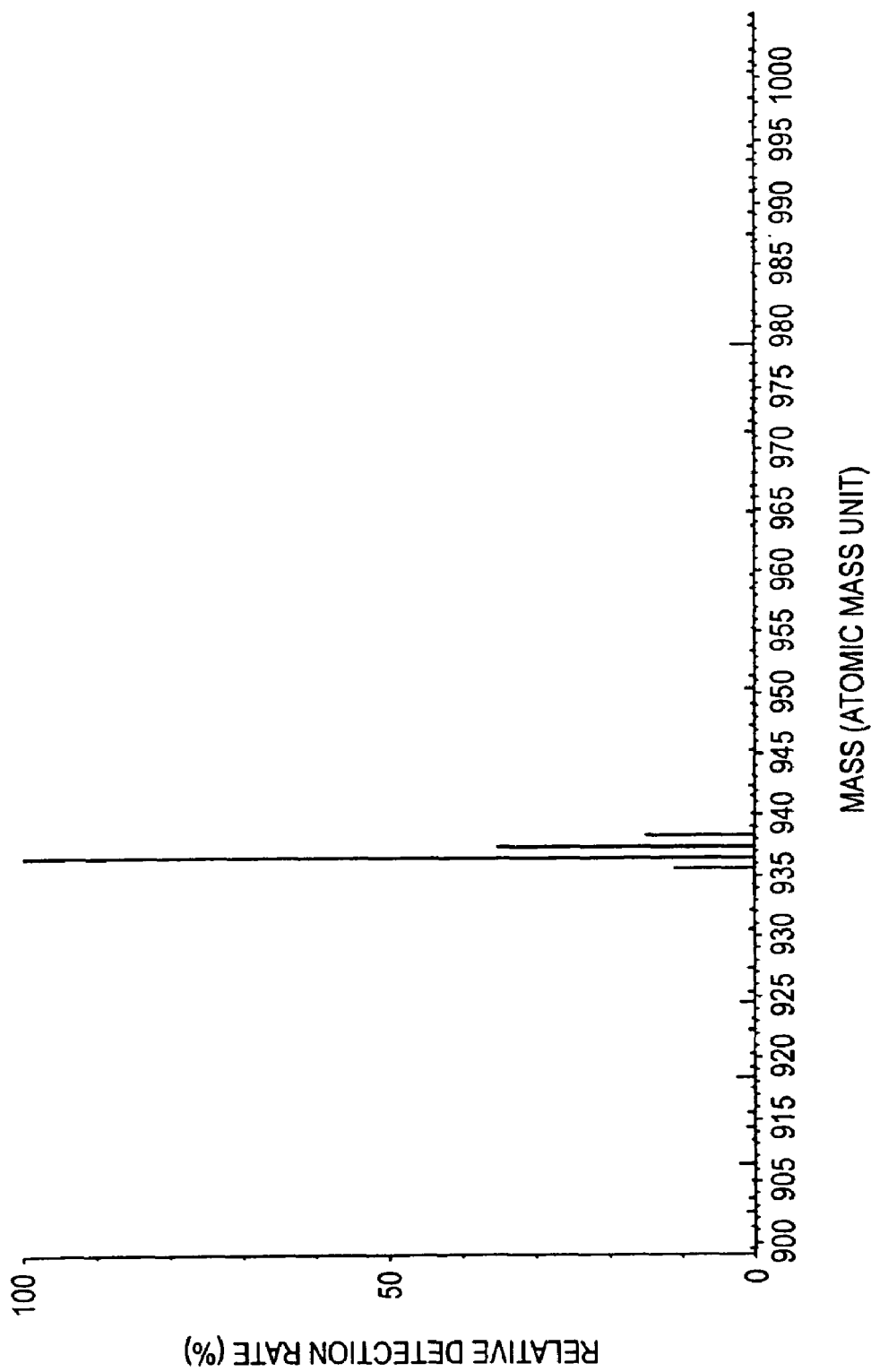

LUBRICANT, RECORDING MEDIUM AND CARBOXYLIC ACID COMPOUND

The present application claims priority to Japanese Patent Application JP2003-356432, filed in the Japanese Patent Office Oct. 16, 2003, and Japanese Patent Application JP2004-242050, filed Aug. 23, 2004; the entire contents of which are incorporated herein by reference.

BACKGROUND OF THE INVENTION

1. Field of the Invention

The present invention relates to a lubricant to be used in a magnetic recording medium or the like, a recording medium using the lubricant, and a carboxylic acid type compound constituting the lubricant.

2. Description of the Related Art

As for a conventional recording medium, for example, a magnetic recording medium, a so-called metallic thin film type magnetic recording medium in which a ferromagnetic metallic material is deposited on a non-magnetic supporting body by a technique of evaporation or the like to allow the ferromagnetic metallic material to be a magnetic layer, or a so-called coating type magnetic recording medium in which a magnetic coating material comprising extremely fine magnetic particles and a resin binder is applied on a non-magnetic supporting body to be a magnetic layer has been known.

These conventional magnetic recording media have a substantially large contact area against a sliding member such as a magnetic head or a guide roller, since a surface of the magnetic layer thereof is extremely smooth, a friction coefficient becomes large and, then, an adhesion phenomenon (so-called adherence) tends to be generated; therefore, there are many problems in that they are insufficient in a traveling property, durability and the like.

Further, since a metal is used in the magnetic layer, the magnetic layer is corroded with passage of time due to a high-temperature, high-humidity environment or presence of a corrosive gas and, accordingly, there is a risk of impairing reliability of data storage.

In order to improve these problems, applications of various types of lubricants have been studied and many trials for suppressing friction and preventing corrosion of the magnetic layer by allowing higher fatty acids, esters thereof or the like to be internally added in the magnetic layer of the magnetic recording medium or applied thereon as a topcoat have been conducted in the past.

However, from the standpoint of properties of the lubricant to be used in the magnetic recording medium or the like, extremely severe characteristics are required in the lubricant. Namely, the lubricant to be used in the magnetic recording medium is required to be:

(1) excellent in low temperature characteristics in order to secure a predetermined lubricating effect when it is used in a cold district;

(2) capable of being applied extremely thinly due to a problem of spacing between a magnetic head and, simultaneously, exerting sufficient lubricating characteristics;

(3) durable for a long time (period) usage and capable of maintaining an lubricating effect during that time (period); and (4) capable of preventing corrosion of the magnetic layer for a long period of time.

The lubricant such as the higher fatty acid, the ester thereof or the like which has conventionally been used is hardly said to fully satisfy such performances as described above and is unsatisfactory in practical characteristics such that, in a field of the magnetic recording medium, for example, a decline in a playback output level is caused by an insufficient ability of the lubricant to be used at a shuttle traveling test.

Further, by adopting a ferromagnetic metallic thin film, it has become necessary to provide lubrication of high precision to sliding between a magnetic tape or a magnetic disc and a magnetic head. For example, in the magnetic tape or the magnetic disc, a lubricant layer is extremely thinly formed on a surface of a magnetic layer in order to realize a high output by minimizing a loss of spacing between the magnetic recording medium and the magnetic head while securing durability and reliability of a vapor-deposited tape or hard disc. As for materials to form such lubricant layer as described above, it is required that a material having an excellent lubricating property is developed.

As for lubricants for metallic thin film type magnetic recording medium, a monocarboxylic acid having a fluoroalkyl ether group, a monocarboxylic acid having a perfluoropolyether ester structure or the like is proposed.

In Patent Document 1 to be described below, as for the lubricant for the metallic thin film type magnetic recording medium, a fluorine-containing alkyl succinic acid diester as shown in the following general formula (9) is proposed; however, this fluorine-containing alkyl succinic acid diester has a problem in that it has a large friction coefficient:

$$R^1\text{—CH}(COOR^2)CH_2COOR^3 \quad (9),$$

wherein $R^1$ represents an aliphatic alkyl group or aliphatic alkenyl group; and one of $R^2$ and $R^3$ represents a fluoroalkyl ether group while the other one of $R^2$ and $R^3$ represents any one of a fluoroalkyl group, a pluoroalkenyl group, a fluorophenyl group, an aliphatic alkyl group and an aliphatic alkenyl group.

In Patent Document 2 to be described below, esters of a fluorine-containing hydrocarbon dicarboxylic acid are proposed as lubricants as shown in following general formulae (10) to (12); however, since a compound as shown in the general formula (10) has only one carboxyl group having a large polarity and, in compounds as shown in the general formulae (11) and (12), a polar group is only an ester bond, all of these compounds have a problem in that they have a large friction coefficient:

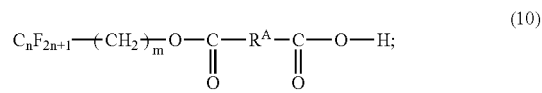

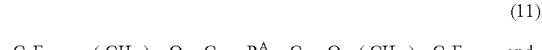

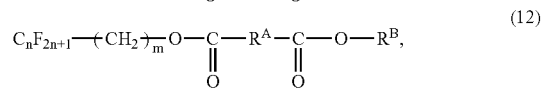

wherein $R^A$ and $R^B$ each represent a hydrocarbon group; and $n \geqq 3$ and $0 \leqq m \leqq 5$.

In Patent Document 3, a dicarboxylic acid containing organic groups $A^1$ and $A^2$ as shown in the following general formula (13) and having two ester bonds as shown in the following general formula (14) is proposed; however, there is a problem in that, since a hydrocarbon chain exists in each of terminals, fluorination effect is small and, accordingly, durability of a shuttle is deteriorated:

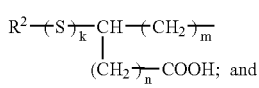

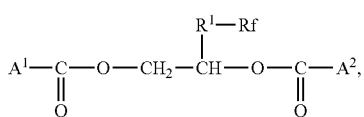

wherein Rf represents a fluorine-containing hydrocarbon group;

$R^1$ represents a hydrocarbon group; and $R^2$ in one of $A^1$ and $A^2$ represents a hydrocarbon group while $R^2$ in the other one of $A^1$ and $A^2$ represents a hydrogen atom or a hydrocarbon group.

Patent Document 1: JP-A No. 6-41561 (pp. 3 to 5);
Patent Document 2: JP-B No. 8-16979 (pp. 2 and 3); and
Patent Document 3: JP-A No. 2001-55593 (pp. 2 to 4).

SUMMARY OF THE INVENTION

Under these circumstances, it is an object of the present invention to provide a lubricant capable of holding an excellent lubricating property under various types of service conditions, maintaining a lubricating effect for a long period of time and providing excellent traveling property, abrasion resistance, durability and the like, a recording medium using the lubricant and a carboxylic acid type compound constituting the lubricant.

Namely, the present invention relates to a carboxylic acid type compound having at least two carboxyl groups and one ester group as represented by the following general formula (1), relates to a lubricant comprising the carboxylic acid type compound and, further, relates to a recording medium in which the lubricant is contained on or in a recording layer:

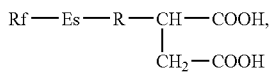

wherein Rf represents a non-substituted or substituted, saturated or unsaturated fluorine-containing hydrocarbon group or hydrocarbon group;

Es represents an ester bond; and

R may be omitted or represent a non-substituted or substituted, saturated or unsaturated hydrocarbon group.

Since, in the carboxylic acid type compound according to the present invention, a carboxyl group is connected to each of two adjacent carbon atoms to each other in one of terminals of the molecule, the compound can firmly be connected to the recording layer or a protective film (for example, carbon film) thereof by means of these two carboxyl groups. On the other hand, on the other terminal of the molecules, a fluorine-containing hydrocarbon group or a hydrocarbon group Rf which reduces a surface energy to realize excellent lubricating characteristics exists.

As a result, when the lubricant comprising the carboxylic acid type compound is contained in the recording layer or the protective film thereof, not only the molecule of the carboxylic acid type compound is firmly connected to the recording layer, a recording material or the protective film thereof at a terminal of a carboxyl group, but also the fluorine-containing hydrocarbon group or the hydrocarbon group which exists at the other terminal of the molecule is effectively aggregated with those in other molecules to form a hydrophobic group layer which realizes a high lubricating action by a coagulation force generated between hydrophobic groups on the side of the surface. For this account, since the lubricant is firmly held by the recording layer, the recording material or the protective film thereof, it is not eliminated from a sliding face even under a severe environment such as low temperature and low humidity and, accordingly, it can be applied in an extremely thin manner and can retain a sufficient lubricating effect for a long period of time.

As a result, when the lubricant is applied in, for example, a magnetic recording medium, it can secure excellent sliding characteristics based on a high lubricating performance, reduce a magnetic head smudge or a dropout to be caused by an abrasion between the magnetic head and the magnetic recording medium and substantially enhance durability and a traveling property of the magnetic recording medium. Particularly, in the magnetic recording medium, when the lubricant comprising the carboxylic acid type compound according to the present invention is applied on a carbon film layer which is the protective film, a carboxyl group and an ester group which are each a polar group is adhered to a surface of the layer to form an excellent lubricating layer thereon.

Further, in a conventional lubricant, a compound having a relatively large polarity such as a carboxylic acid, an amine or an amine salt of a carboxylic acid is, though small in a friction coefficient, inclined to be inferior in still durability while a compound having a relatively small polarity such as an ester compound is, though excellent in the still durability, inclined to increase the friction coefficient. The carboxylic acid type compound according to the present invention contains two carboxyl groups and at least one ester bond as terminal polar groups and, accordingly, can simultaneously realize a reduction of the friction coefficient and excellent sill durability in a well balanced manner.

The carboxylic acid type compound according to the present invention is a novel substance and, when the lubricant comprising the substance is used as a lubricant for a recording medium, for example, a lubricant for a magnetic recording medium, an excellent lubricating property can be held under various types of service conditions, a-lubricating effect can be maintained for a long period of time and can provide a recording medium having excellent traveling property, abrasion resistance, durability and the like.

Further, since a conventional fluorine-containing lubricant is only soluble in a fluorine type solvent, when it is applied, the fluorine type solvent is essential, whereas the carboxylic acid type compound is soluble in a hydrocarbon type solvent such as toluene or acetone and, accordingly, it can, for example, be applied by using any one of these solvents. Since the hydrocarbon type solvent is easier in waste disposal than the fluorine type solvent, the hydrocarbon type solvent puts a small load to an environment at the time of usel and is, accordingly, preferred.

According to the present invention, the carboxylic acid type compound is preferably a carboxylic acid type compound as represented by the following general formula (2):

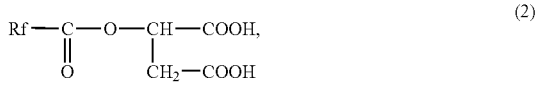

$$Rf-\underset{O}{\overset{\parallel}{C}}-O-\underset{CH_2-COOH}{\overset{|}{CH}}-COOH, \quad (2)$$

wherein Rf represents a non-substituted or substituted, saturated or unsaturated fluorine-containing hydrocarbon group or hydrocarbon group.

Further, the carboxylic acid type compound is also preferably a carboxylic acid type compound as represented by the following general formula (3):

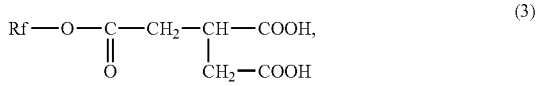

$$Rf-O-\underset{O}{\overset{\parallel}{C}}-CH_2-\underset{CH_2-COOH}{\overset{|}{CH}}-COOH, \quad (3)$$

wherein Rf represents a non-substituted or substituted, saturated or unsaturated fluorine-containing hydrocarbon group or hydrocarbon group.

Further, according to the present invention, the lubricant is preferably a lubricant comprising a carboxylic acid type compound as represented by the general formula (2) or (3) or a mixture of lubricants as represented by the general formulae (2) and (3).

According to the present invention, the carboxylic acid type compound as represented by the general formula (1) may be synthesized by any method and can be synthesized, for example, by an ester reaction between a compound having an Rf group and a compound in which a carboxyl group is connected to each of a terminal carbon atom and an adjacent carbon atom thereto. The carboxylic acid type compound as represented by the general formula (2) or (3) can be synthesized, for example, in a manner as described below.

Namely, the compound as represented by the general formula (2) can be synthesized by a following condensation reaction such that a carboxylic acid chloride containing an Rf group and malic acid are mixed with each other and, then, heated at 100° C.:

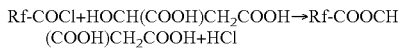

Rf-COCl+HOCH(COOH)CH$_2$COOH→Rf-COOCH (COOH)CH$_2$COOH+HCl

After the reaction is terminated, the resultant reaction product is rinsed with an organic solvent or an inorganic solvent and, then, rinsed in a separating manner by using a separating funnel and, thereafter, an impurity or an unnecessary material is removed through recrystallization purification or the like by using 2-propanol (isopropyl alcohol; IPA) and n-hexane, to thereby obtain a subject carboxylic acid type compound of high purity.

Further, as for the compound as represented by the general formula (3), an alcohol containing an Rf group and 1,2,3-propane tricarboxylic acid are dissolved in toluene and, then, subjected to the following condensation reaction by reflux heating to synthesize a product and, thereafter, the thus-synthesized product is purified in a same manner as described above, to thereby obtain a subject carboxylic acid type compound of high purity:

Rf-OH+HOOCCH$_2$CH(COOH)CH$_2$COOH+Rf-OCOCH$_2$CH(COOH)CH$_2$COOH+H$_2$O

As described above, when the lubricant comprising the carboxylic acid type compound as represented by the general formula (1) is applied on the recording layer or the protective film thereof, the lubricating action is realized by the coagulation force generated between the fluorine-containing hydrocarbon group which is a hydrophobic group and the hydrocarbon group Rf. When the Rf group is a fluorine-containing hydrocarbon group, it preferably has from 6 to 50 carbon atoms in total and from 4 to 20 carbon atoms in a fluorinated hydrocarbon group. The Rf group may be a saturated or unsaturated, linear, branched or cyclic chain and is particularly preferably a saturated linear chain.

For example, when the Rf group is a hydrocarbon group, it is preferably a group as represented by the following general formula (4):

$$CH_3-(CH_2)_l- \quad (4),$$

wherein l represents an integer selected from the range of from 8 to 30 and, preferably, from 12 to 20.

Further, when the Rf group is a fluorine-containing hydrocarbon group, it is preferably a group as represented by the following general formula (5):

$$CF_3-(CF_2)_n-(CH_2)_m- \quad (5),$$

wherein m and n are each an integer selected from the following respective ranges:

m=2 to 20; and n=3 to 18 and, preferably, m=4 to 13; and n=3 to 10.

The fluorinated hydrocarbon group may be concentrated on one position as described above or be dispersed as shown in the following general formula (6); in this case, not only a —CF$_3$ or —CF$_2$— group, but also a —CHF$_2$, —CHF— group or the like is permissible:.

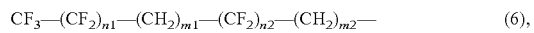

$$CF_3-(CF_2)_{n1}-(CH_2)_{m1}-(CF_2)_{n2}-(CH_2)_{m2}- \quad (6),$$

wherein n1+n2=n; and
m1+m2=m.

The reason why the number of carbon atoms is restricted in each of the general formulae (4), (5) and (6) is that, when the number of carbon atoms (l, or a sum of m and n) which constitute an alkyl group or a fluorine-containing alkyl group is the aforementioned minimum or more, length thereof becomes appropriate, a coagulation force generated between hydrophobic groups is effectively performed, an excellent lubricating action is realized and, then, friction/abrasion resistance can be enhanced and, further, when the number of carbon atoms thereof is the maximum or less, solubility of the lubricant comprising the carboxylic acid type compound in the solvent is favorably maintained.

Particularly, when the Rf group contains a fluorine atom, it is effective in reduction of the friction coefficient and, further, an improvement of a traveling property or the like. However, it is preferable to prevent a hydrolysis from being generated by securing stability of an ester bond such that a hydrocarbon group is provided between the fluorine-containing hydrocarbon group and an ester bond to separate the fluorine-containing hydrocarbon group from the ester bond.

Further, it is also permissible that the Rf group contains a fluoroalkyl ether group or a perfluoropolyether group.

The R group may be omitted; however, when it exists, it is preferably a hydrocarbon chain having a relatively small number of carbon atoms.

Further, the Rf group or the R group contains an element such as nitrogen, oxygen, sulfur, phosphorous, halogen or the like as a constitutional element and, in addition to the aforementioned functional group, may further contain any one of a hydroxyl group, a carboxyl group, a carbonyl group, an amino group, an ester group and the like.

The carboxylic acid type compound having such constitution as described above is provided with advantages such that, since it is soluble in a non-fluorine type solvent which puts a small load to the environment, it can be applied, dipped, sprayed or the like by using a general-purpose solvent such as a hydrocarbon type solvent, a ketone type solvent, an alcoholic solvent or an ester type solvent. Specific examples of such solvents include hexane, heptane, octane, decane, dodecane, benzene, toluene, xylene, cyclohexane, methyl ethyl ketone, methyl isobutyl ketone, methanol, ethanol, isopropanol, diethyl ether, tetrahydrofuran, dioxane and cyclohexanone.

Further, the lubricant is preferably a lubricant for a recording medium and, particularly, the recording medium is a recording medium having a magnetic layer and the lubricant is preferably contained on the magnetic layer, in the magnetic layer, or on and in the magnetic layer.

Particularly, when the carboxylic acid type compound is applied as the lubricant on a carbon film layer provided as a protective film on the magnetic layer, two carboxyl groups and at least one ester bond which each are a polar group portion of the lubricant molecule are adsorbed on the carbon film layer and, then, a lubricant layer having an excellent durability can be formed by a coagulation force generated between hydrophobic groups.

Further, the recording medium according to the present invention is provided with a layer containing the lubricant in some way or other. For example, when the recording medium is a magnetic recording medium, it is a so-called metallic thin film type magnetic recording medium in which a ferromagnetic metallic material is deposited on a non-magnetic supporting body by evaporation or the like to be a magnetic layer, a so-called coating type magnetic recording medium in which a magnetic coating material comprising extremely fine magnetic particles and a resin binder is applied on a non-magnetic supporting body to be a magnetic layer, or the like. In these media, the layer comprising the lubricant may be a layer to coat a surface of the magnetic recording medium or may internally added to the magnetic layer.

Further, various types of additives, for example, a rust inhibitor, may optionally be mixed in the lubricant. As for such rust inhibitors as described above, articles which have conventionally been used in the magnetic recording medium are permissible. Examples thereof include phenols, naphthols, quinones, nitrogen-containing heterocyclic compounds, oxygen-containing heterocyclic compounds and sulfur-containing heterocyclic compounds.

When any one of the rust inhibitors is employed, it may be made up to be a composite with the lubricant and used; however, in a case in which, after the rust inhibitor is applied on the carbon film layer, the lubricant is applied on the thus-applied rust inhibitor to form a two-layer constitution, a rust inhibiting effect is enhanced and, accordingly, the case is preferred.

On this occasion, the non-magnetic supporting body is not particularly limited and can adopt a conventional one. For example, a flexible substrate such as a plastic film or a rigid substrate such as glass is permissible. When a substrate having rigidity such as an aluminum alloy plate or a glass plate is used as the non-magnetic supporting body, it is permissible to form an oxide film such as an anodized aluminum film or a nickel-phosphorous film on a surface of the substrate and allow the surface to be hard. Further, optionally, an underlying layer may be formed between the non-magnetic supporting body and the magnetic layer.

The carboxylic acid type compound according to the present invention is, as described above, preferably used as the lubricant for the recording medium and, among other things, the magnetic recording medium. However, the lubricant can be used not only in the magnetic recording medium, but also in an optical recording medium and, further, the supporting body can be used not only in a tape, but also in a recording medium such as a disc medium, for example, a magnetic disc or an optical disc.

BRIEF DESCRIPTION OF THE DRAWINGS

FIG. 9 is a graph showing a mass spectrometry spectrum of a carboxylic acid type compound of Example 4 according to the present invention.

DETAILED DESCRIPTION OF THE INVENTION

Hereinafter, taking, for example, a case in which "a lubricant" is used for a magnetic recording medium, preferred embodiments according to the present invention will be described with reference to the accompanying drawings.

Figure 1:
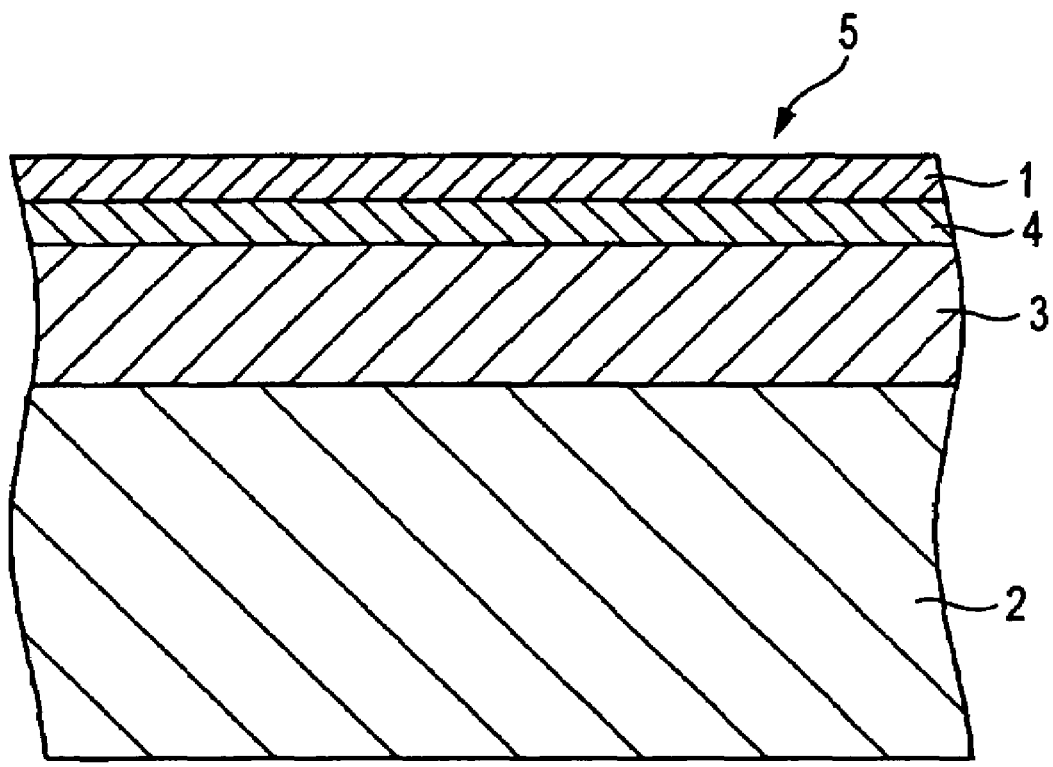
FIG. 1 is a schematic cross-sectional diagram of a metallic thin film type magnetic recording medium based on a preferred embodiment according to the present invention.

FIG. 1 is a schematic cross-sectional diagram of a metallic thin film type magnetic recording medium 5. In this magnetic recording medium 5, at least a magnetic layer 3 comprising a metallic magnetic thin film formed by an evaporation technique or the like, a carbon film layer 4 and a lubricant layer 1 containing a carboxylic acid type compound are formed on a non-magnetic supporting body 2 in the stated order. Further, optionally, an underlying layer maybe formed between the non-magnetic supporting body and the magnetic layer.

The non-magnetic supporting body 2 is not particularly limited and can adopt a conventional one. For example, a flexible substrate such as a plastic film or a rigid substrate such as glass is permissible. Further, an article subjected to surface hardening processing or the like is also permissible.

The metallic magnetic thin film constituting the magnetic layer 3 is also not particularly limited and can adopt a conventional one. For example, an article formed by a plating, sputtering or vacuum evaporation technique or the like as a continuous film such as an in-plane magnetized recording metallic magnetic thin film comprising a metal such as Fe, Co or Ni, a Co—Ni type alloy, a Co—Pt type alloy, a Co—Pt—Ni type alloy, an Fe—Co type alloy, an Fe—Ni type alloy, an Fe—Co—Ni type alloy, an Fe—Ni—B type alloy, an Fe—Co—B type alloy or an Fe—Co—Ni—B type alloy, or a Co—Cr type alloy magnetic thin film can be mentioned.

Particularly, when the in-plane magnetized metallic magnetic thin film is adopted, an underlying layer comprising a non-magnetic material having a low melting point such as Bi, Sb, Pb, Sn, Ga, In, Ge, Si or Tl is previously formed on the non-magnetic supporting body and, then, any one of the metals is applied on the thus-formed underlying layer by an evaporation or sputtering technique from a direction perpendicular to the underlying layer to allow the non-magnetic material having a low melting point to be dispersed in the metallic magnetic thin film and, then, not only an in-plane isotropy may be secured by canceling an alignment property but also an antimagnetic property may be enhanced.

The magnetic layer 3 in which a ferromagnetic metallic material is deposited on the non-magnetic supporting body by an evaporation technique or the like is formed by deposition of the magnetic material and, further, since a binder is not used in the magnetic layer, it is brittle and, then, in order to compensate such brittleness, a protective film layer 4 such as a carbon film is provided.

As for the protective film layer 4, besides the carbon film, for example, a silicon oxide ($SiO_2$) film or a zirconia ($ZrO_2$) film may be used. Further, the lubricant layer 1 is preferably applied on the carbon film 4 but may be applied on the magnetic layer 3 comprising the metallic magnetic thin film in a direct or indirect manner.

As for a forming method for the carbon film layer 4, the sputtering is ordinarily performed; however, the method is not particularly limited and any one of known methods, for example, a CVD (chemical vapor deposition) method using a hydrocarbon gas can be adopted. Thickness of the carbon film layer 4 is preferably from 2 to 100 nm and, more preferably, from 5 to 30 nm. Further, the carbon film may also be an amorphous carbon film having a diamond structure or a graphite structure as denoted as a hard carbon film or a diamond-like carbon.

The lubricant layer 1 can be formed by applying a lubricant comprising the carboxylic acid type compound according to the present invention on the carbon film layer 4 as a topcoat. An amount of the lubricant to be applied is, for example, preferably from 0.3 to 100 mg/m$^3$ and, more preferably, from 0.5 to 20mg/m$^3$. When the lubricant is applied, it can be dissolved in an organic solvent such as hexane and, then, used. When the amount thereof to be applied is unduly small, effects of reduction of friction coefficient and enhancement of abrasion resistance/durability are not realized, while, when it is unduly large, an adhesion phenomenon is generated between a sliding member and a ferromagnetic metallic thin film, which deteriorates a traveling property to the contrary.

The lubricant according to the present invention can be applied on the protective film extremely thinly and, on this occasion, can exhibit sufficient lubricating characteristics and maintain a lubricating effect durable for a long-term service.

Figure 2:
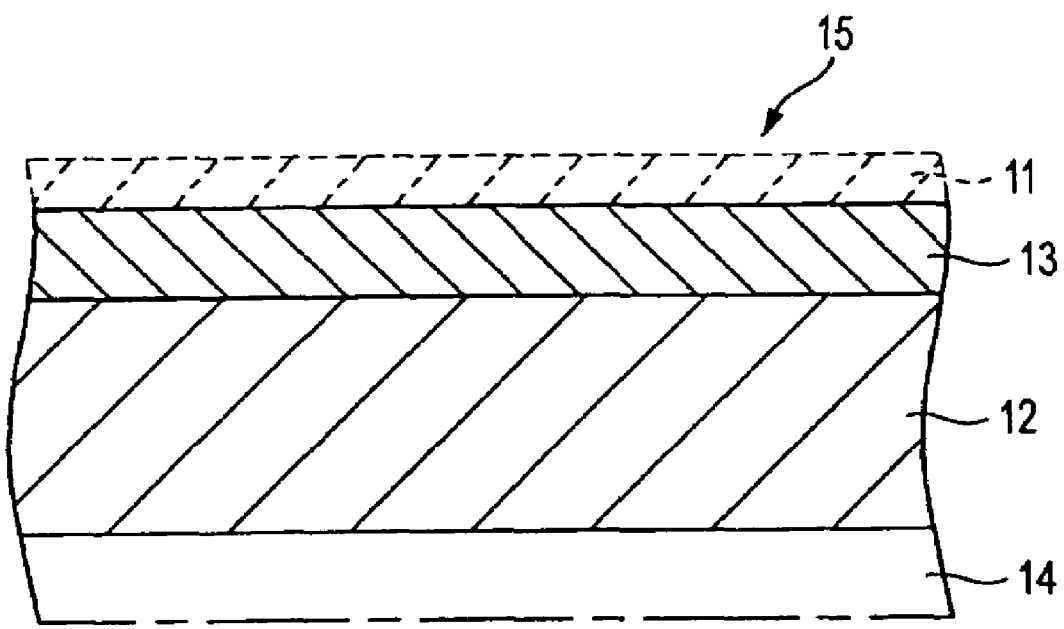
FIG. 2 is a schematic cross-sectional diagram of a coating type magnetic recording medium based on a preferred embodiment according to the present invention.

FIG. 2 is a schematic cross-sectional diagram of a coating type magnetic recording medium 15. In this magnetic recording medium 15, a magnetic coating material comprising fine magnetic particles and a resin binder is applied on a non-magnetic supporting body 12 to be a magnetic layer 11.

In a case of the coating type, an internal addition type in which a predetermined amount of the lubricant is allowed to be contained in the magnetic layer 11 comprising magnetic particles and a binder is also permissible. Further, a lubricating layer 13 (shown as a dotted line which is a phantom line in FIG. 2) may be formed by applying the lubricant on a surface of the magnetic layer 11 by interposing or without interposing a protective film in a same manner as in the thin film type. When the lubricant is allowed to be contained in the magnetic layer 11 of the coating type magnetic recording medium 15, an amount thereof is, based on the entire mass of the magnetic particles 100, preferably from 0.5 to 10% by mass.

As for the magnetic particles, ferromagnetic powder is preferred; oxide magnetic powder of, for example, ferrites as represented by γ-$Fe_2O_3$, Co-containing γ-$Fe_2O_3$, γ-$Fe_2O_3$ coated with Co, $CrO_2$ and magnetite, and metallic magnetic powder comprising, as main components, Fe, Co, Ni and the like such as alloy powder of, for example, Fe—Al type, Fe—Al—Ni type, Fe—Al—Ca type, Fe—Al—Co type, Fe—Al—Zn type, Fe—Ni type, Fe—Ni—Si—Al—Mn type, Fe—Ni—Si—Al—Zn type, Fe—Mn—Zn type and Ni—Co type can be used.

Further, as for the binders, a polyester resin, a polyurethane resin, a polyvinyl chloride resin such as a polyvinyl chloride copolymer and the like are representative. Still further, for the purpose of enhancing dispersibility of the magnetic powder to these binder resins, these resins preferably contain at least one polar group selected from among —$SO_3M$, —$OSO_3M$, —COOM, —$PO(OM')_2$ (M representing an alkali metal such as Na, K, Li or the like; M' representing a hydrogen atom, an alkali metal or an alkyl group) and a sulfobetaine group as a repeating unit.

Further, a known additive such as a polishing agent, a lubricant, a curing agent or an antistatic agent may be included in the magnetic layer 11 comprising the binder and the magnetic powder.

Further, as for the non-magnetic supporting body 12 to be used for the metallic magnetic thin film type or coating type magnetic recording medium, a known material can appropriately be used. Examples of such known materials include polyesters such as polyethylene terephthalate and polyethylene naphthalate; polyolefins such as polypropylene; cellulose derivatives such as cellulose triacetate and cellulose diacetate; aramid resins such as polyaramid; and plastics such as polycarbonate.

These non-magnetic supporting bodies may be of monolayer structure or multi-layer structure. Further, they may be subjected to a corona discharge treatment or the like. Still further, they can be formed in an arbitrary shape such as a film shape, a sheet shape, a disc shape or a card shape.

Still further, a backcoat layer 14 may be provided on a face on the side on which the magnetic layer 13 is not provided of the non-magnetic supporting body 12. The backcoat layer 14 can be formed in accordance with an ordinary method.

Figure 3:
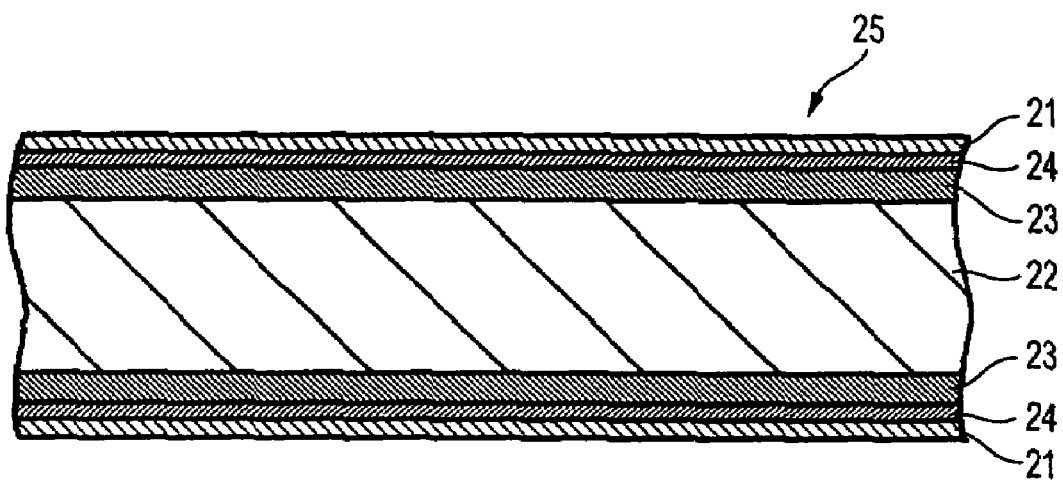
FIG. 3 is a schematic cross-sectional diagram of a disc type magnetic recording medium based on a preferred embodiment according to the present invention.
Figure 4:
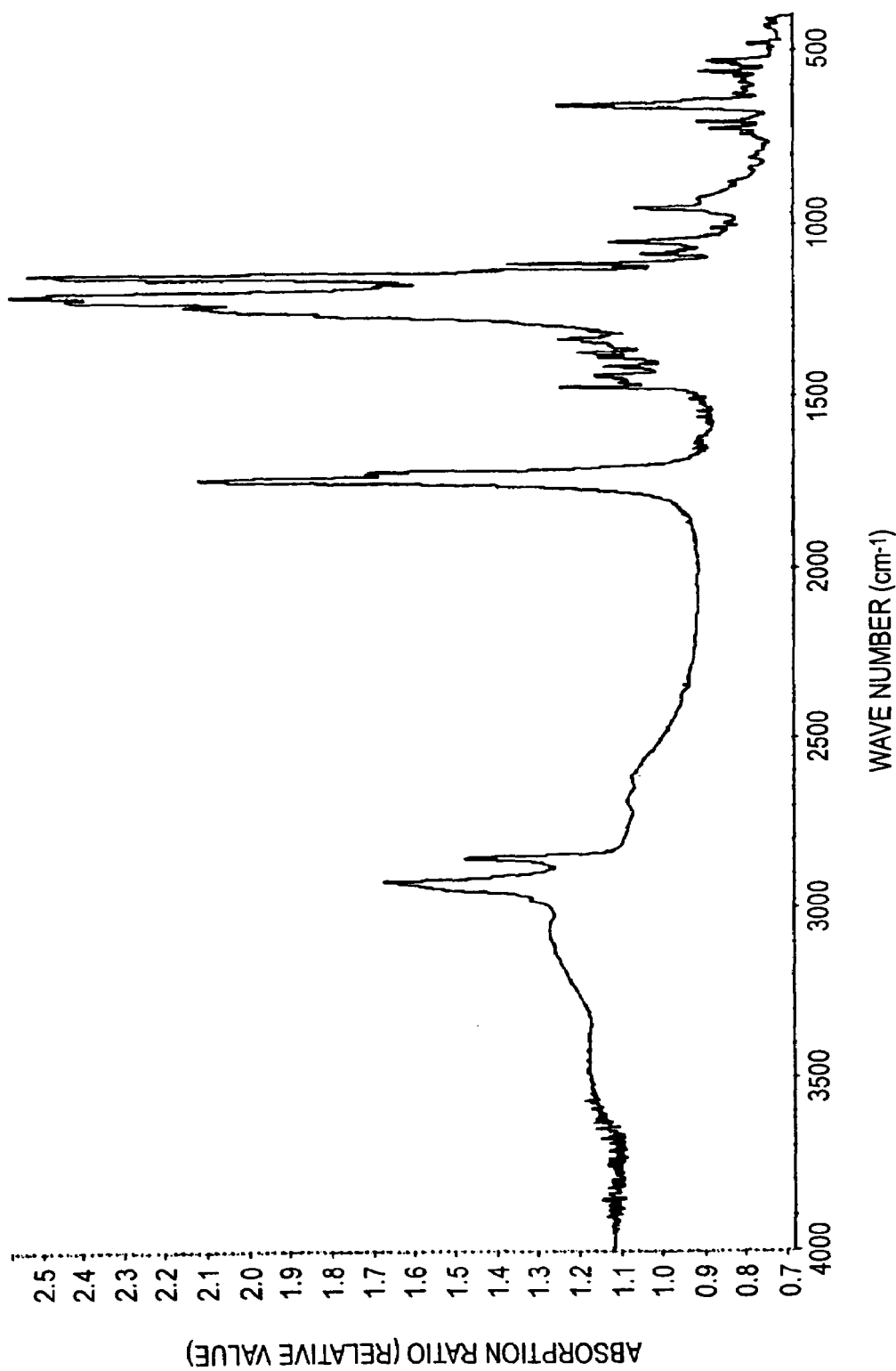
FIG. 4 is a graph showing an infrared light absorption spectrum of a carboxylic acid type compound of Example 1 according to the present invention.
Figure 5:
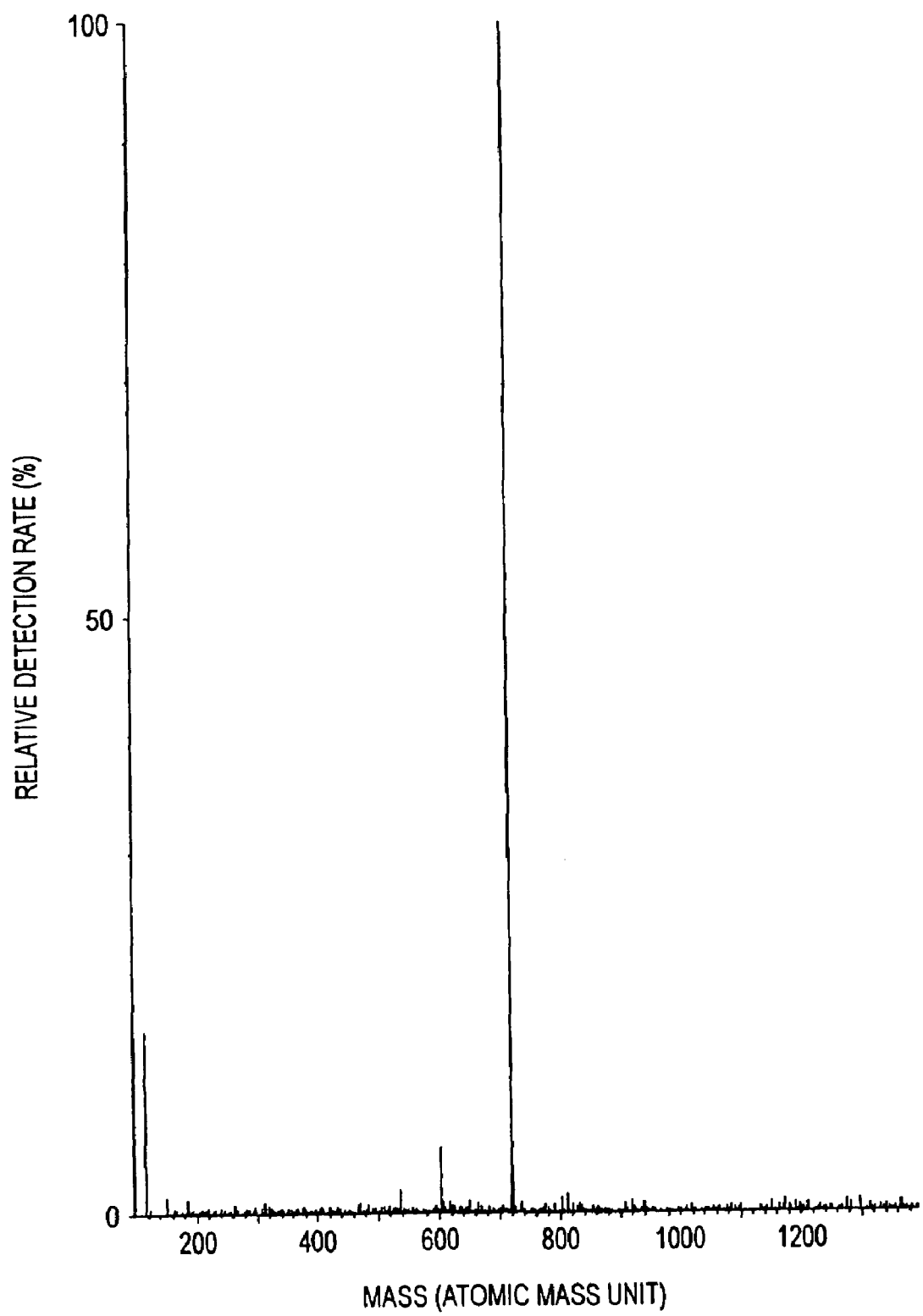
FIG. 5 is a graph showing a mass spectrometry spectrum of a carboxylic acid type compound of Example 1 according to the present invention.

FIG. 3 shows a magnetic recording medium 25 in which a magnetic layer 23 comprising a ferromagnetic metallic thin film, a protective film 24 comprising a carbon film or the like and a lubricant layer 21 are formed on both faces of a flexible non-magnetic supporting body 22 in disc form in the stated order. Also in this case, the magnetic layer 23 is formed by coating and a lubricant can internally be added to the magnetic layer 23.

Embodiments

Hereinafter, the present invention will be described in detail by Examples and Comparative Examples, but is by no means limited thereto.

Firstly, compounds of Examples 1 to 20 as shown in Tables 1 and 2 were synthesized as described below. Each of the compounds of Examples 12 to 20 as shown in Table 2 ha a same fundamental constitution as that of a compound in each of Examples 1 and 2 and is an example in which only the number of carbon atoms constituting a fluorinated alkyl group or hydrocarbon chain thereof is different from that of the compound in each of Examples 1 and 2 in various ways.

the resultant mixture was cooled by ice to allow a subject article to be precipitated as a crystal. The crystal was collected by filtration and, accordingly, the purified subject article was obtained. A yield thereof was about 50%.

When a product, namely, the subject article, was measured by using an infrared absorption spectrum (IR) method and a liquid chromatography mass spectrometry (LCMS), respective results thereof were obtained as shown in FIGS.

TABLE 1

| Example | Carboxylic acid type compound |
|---|---|
| Example 1 | $CF_3(CF_2)_7(CH_2)_{10}COOCH(COOH)CH_2COOH$ |
| Example 2 | $CF_3(CF_2)_3(CH_2)_{10}COOCH(COOH)CH_2COOH$ |
| Example 3 | $C_{17}H_{35}COOCH(COOH)CH_2COOH$ |
| Example 4 | $CF_3(CF_2)_7(CH_2)_2OCOCH_2CH(C_{18}H_{37})COOCH(COOH)CH_2COOH$ |
| Example 5 | $CF_3(CF_2)_7COOCH(COOH)CH_2COOH$ |
| Example 6 | $CHF_2(CF_2)_7COOCH(COOH)CH_2COOH$ |
| Example 7 | $CF_3(CF_2)_7(CH_2)_2OCOCH_2CH(COOH)CH_2COOH$ |
| Example 8 | $CF_3(CF_2)_7(CH_2)_6OCOCH_2CH(COOH)CH_2COOH$ |
| Example 9 | $CF_3(CF_2)_7(CH_2)_{11}OCOCH_2CH(COOH)CH_2COOH$ |
| Example 10 | $CF_3(CF_2)_3(CH_2)_6OCOCH_2CH(COOH)CH_2COOH$ |
| Example 11 | $C_{18}H_{37}OCOCH_2CH(COOH)CH_2COOH$ |

TABLE 2

| Example | Carboxylic acid type compound |
|---|---|
| Example 12 | $CF_3(CF_2)_7(CH_2)_4COOCH(COOH)CH_2COOH$ |
| Example 13 | $CF_3(CF_2)_3(CH_2)_4COOCH(COOH)CH_2COOH$ |
| Example 14 | $CF_3(CF_2)_3(CH_2)_7COOCH(COOH)CH_2COOH$ |
| Example 15 | $CF_3(CF_2)_9(CH_2)_{10}COOCH(COOH)CH_2COOH$ |
| Example 16 | $CF_3(CF_2)_7(CH_2)_{12}COOCH(COOH)CH_2COOH$ |
| Example 17 | $CF_3(CF_2)_5(CH_2)_{10}COOCH(COOH)CH_2COOH$ |
| Example 18 | $CF_3(CF_2)_7CH(C_9H_{19})CH_2CH=CH(CH_2)_7COOCH(COOH)CH_2COOH$ |
| Example 19 | $CF_3(CF_2)_7CH(C_6H_{13})(CH_2)_7COOCH(COOH)CH_2COOH$ |
| Example 20 | $CH_3(CH_2)_3(CH_2CH_2CH(CH_2CH_2(CF_2)_9CF_3))_2(CH_2)_7COOCH(COOH)CH_2COOH$ |

Synthesis of Compound of Example 1

A fluorine-containing carboxylic acid chloride: $CF_3(CF_2)_7(CH_2)_{10}COCl$ as an acid chloride compound containing an Rf group in the general formula (2) was allowed to react with malic acid which is a compound containing a carboxyl group in the general formula (2) in accordance with the following reaction formula to synthesize a compound as shown in Example 1 which is a carboxylic acid type compound according to the present invention in the stated order in synthesis procedures described below:

$CF_3(CF_2)_7(CH_2)_{10}COCl+HOCH(COOH)CH_2COOH \rightarrow CF_3(CF_2)_7(CH_2)_{10}COOCH(COOH)CH_2COOH+HCl$ 60.4 g of 1,1-(perfluorooctyl)undecanoic acid chloride: $CF_3(CF_2)_7(CH_2)_{10}COCl$ and 13.4 g of malic acid: $HOCH(COOH)CH_2COOH$ were mixed in 500 ml of tetrahydrofuran (THF) and heated for 3 hours in a reflux manner to allow them to react with each other.

After such reaction as described above was terminated, THF was filtered out and, then, a resultant reaction product was purified by recrystallization. Namely, a reaction liquid was filtered to separate the reaction product in a solid state from THF and, then, after the reaction product was dissolved in 500 ml of 2-propanol (IPA) heated at 60° C., an impurity was removed by filtration to collect a filtrate which was, subsequently, condensed and, then, after the thus-condensed filtrate was dissolved in 500 ml of hexane heated at 60° C., 4 and 5. From these results, the product was found to be a compound as expressed by the chemical formula:

$CF_3(CF_2)_7(CH_2)_{10}COOCH(COOH)CH_2COOH.$

Synthesis of Compound of Example 9

1,1-(perfluorooctyl)undecanol as an alcohol containing an Rf group in the general formula (3) was allowed to react with 1,2,3-propane tricarboxylic acid which is a compound containing a carboxyl group in the general formula (3) in accordance with the following reaction formula to synthesize a compound as shown in Example 9 in the stated order in synthesis procedures described below:

$CF_3(CF_2)_7(CH_2)_{11}OH+HOOCCH_2CH(COOH)CH_2COOH \rightarrow CF_3(CF_2)_7(CH_2)_{11}OCOCH_2CH(COOH)CH_2COOH+H_2O$ 59.0 g of 1,1-(perfluorooctyl)undecanol: $CF_3(CF_2)_7(CH_2)_{11}OH$ and 17.6 g of 1,2,3-propane tricarboxylic acid: $HOOCCH_2CH(COOH)CH_2COOH$ were mixed in 500 ml of toluene and heated for 3 hours in a reflux manner to allow them to react with each other.

After such reaction as described above was terminated, toluene was filtered out and, then, a resultant reaction product was purified by recrystallization. Namely, a reaction liquid was filtered to separate the reaction product in a solid state from toluene and, then, after the reaction product was dissolved in 500 ml of 2-propanol heated at 60° C., an impurity was removed by filtration to collect a filtrate which was, subsequently, condensed and, then, after the thus-condensed filtrate was dissolved in 500 ml of hexane heated at 60° C., the resultant mixture was cooled by ice to allow a subject article to be precipitated as a crystal. The crystal was collected by filtration and, accordingly, the purified subject article was obtained. A yield thereof was about 60%.

Figure 6:
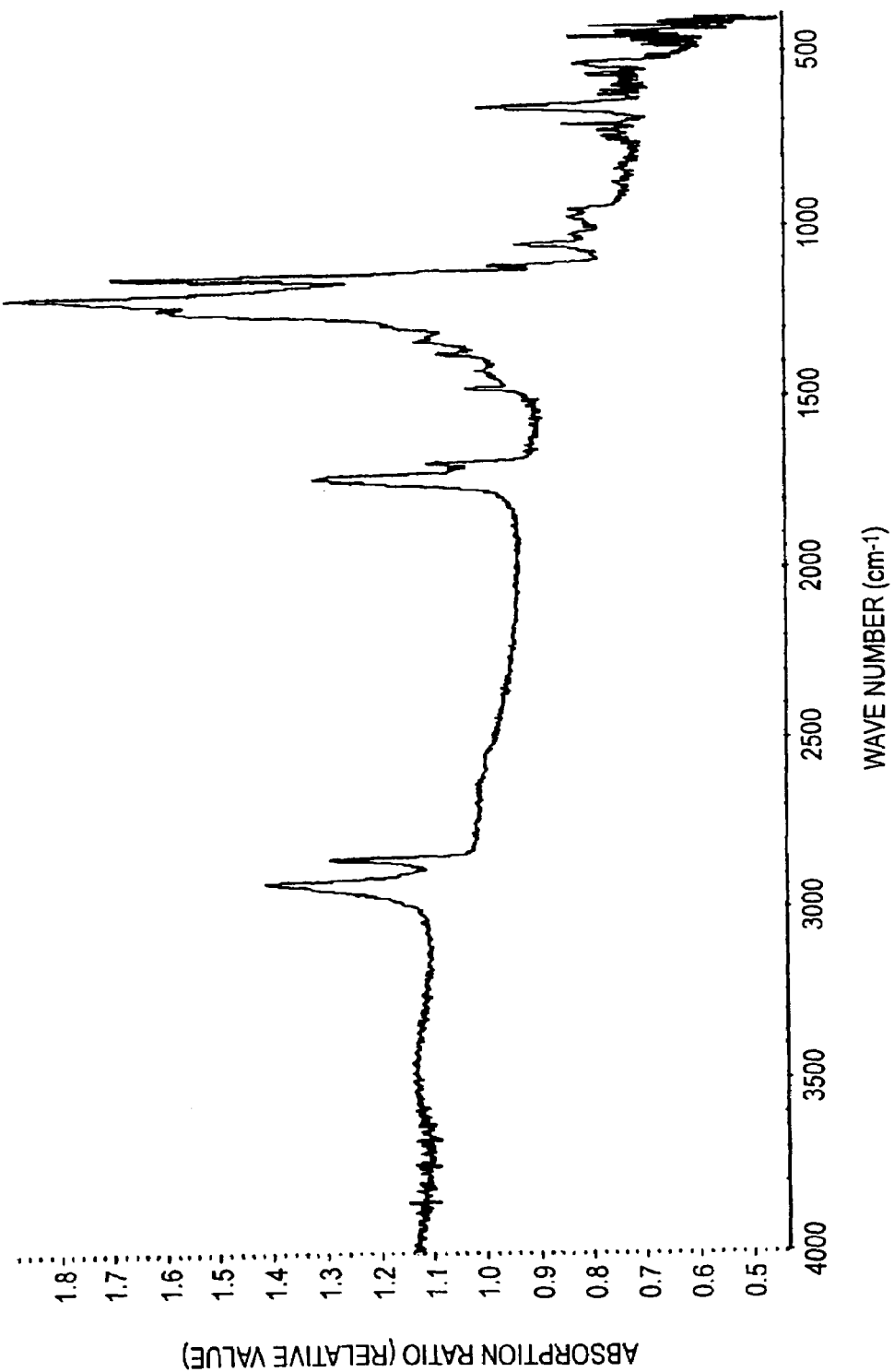
FIG. 6 is a graph showing an infrared light absorption spectrum of a carboxylic acid type compound of Example 9 according to the present invention.
Figure 7:
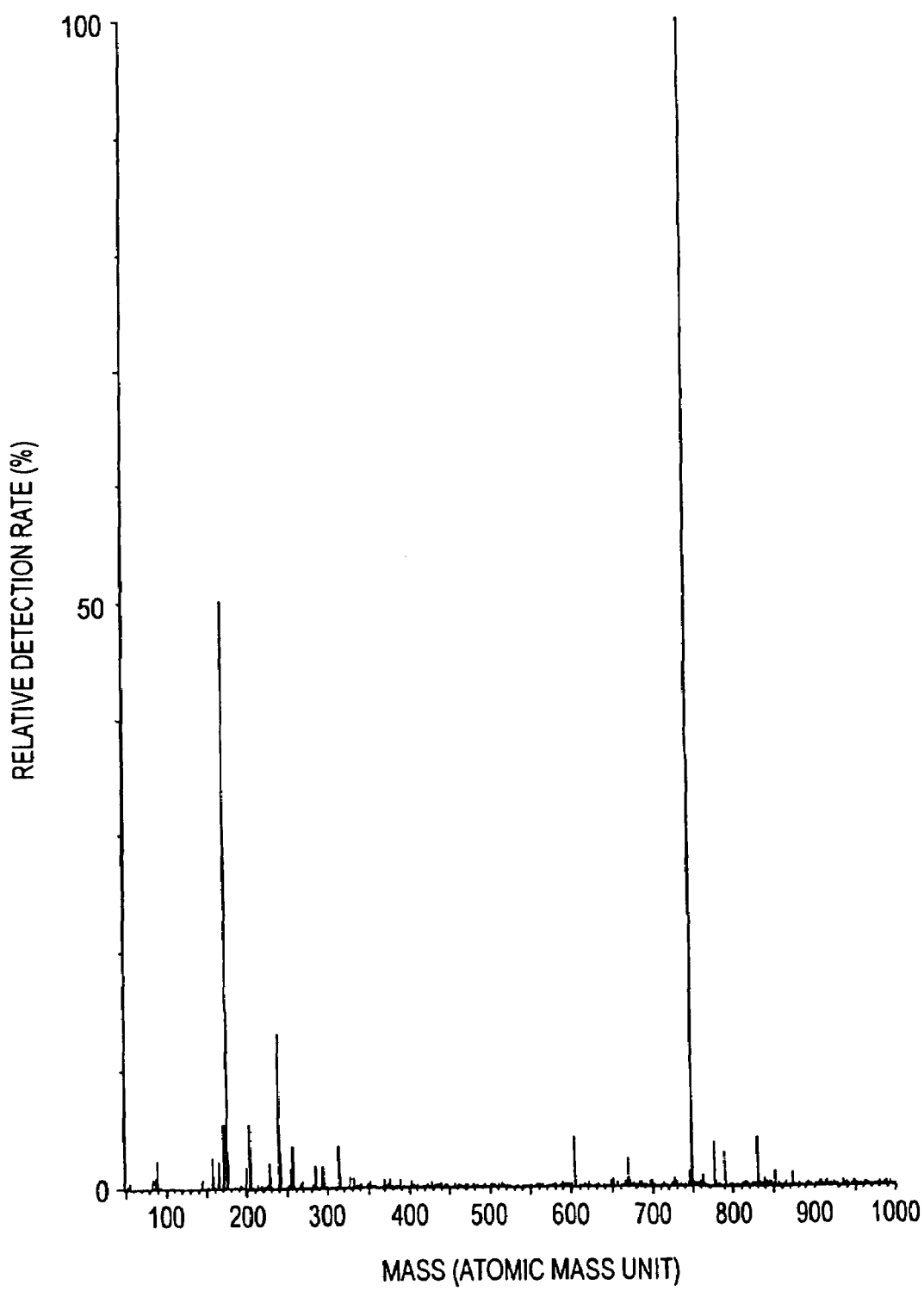
FIG. 7 is a graph showing a mass spectrometry spectrum of a carboxylic acid type compound of Example 9 according to the present invention.

When a product, namely, the subject article, was measured by using an infrared absorption spectrum (IR) method and a liquid chromatography mass spectrometry (LCMS), respective results thereof were obtained as shown in FIGS. 6 and 7. From these results, the product was found to be a compound as expressed by the chemical formula:

$CF_3(CF_2)_7(CH_2)_{11}OCOCH_2CH(COOH)CH_2COOH$.

Further in a same manner as in the aforementioned two examples, a raw material compound having a predetermined group as an Rf group in the general formula (2) or (3) and a carboxylic acid raw material compound were allowed to react with each other, to thereby synthesize carboxylic acid type compounds of Examples 2 to 6 and Examples 12 to 20 or carboxylic acid type compounds of Examples 7, 8, 10 and 11. Reaction substances which have been used in synthesis of compounds of Examples 1 to 20 and reaction yields are collectively shown in Tables 3 and 4.

TABLE 3

| Example | Raw material compound containing Rf | Carboxylic acid raw material compound | Reaction yield (%) |
|---|---|---|---|
| Example 1 | $CF_3(CF_2)_7(CH_2)_{10}COCl$ | $HOCH(COOH)CH_2COOH$ | 60 |
| Example 2 | $CF_3(CF_2)_3(CH_2)_{10}COCl$ | $HOCH(COOH)CH_2COOH$ | 50 |
| Example 3 | $C_{17}H_{35}COCl$ | $HOCH(COOH)CH_2COOH$ | 70 |
| Example 4 | $CF_3(CF_2)_7(CH_2)_2OCOCH_2CH(C_{18}H_{37})COCl$ | $HOCH(COOH)CH_2COOH$ | 60 |
| Example 5 | $CF_3(CF_2)_7COCl$ | $HOCH(COOH)CH_2COOH$ | 10 |
| Example 6 | $CHF_2(CF_2)_7COCl$ | $HOCH(COOH)CH_2COOH$ | 10 |
| Example 7 | $CF_3(CF_2)_7(CH_2)_2OH$ | $HOOCCH_2CH(COOH)CH_2COOH$ | 60 |
| Example 8 | $CF_3(CF_2)_7(CH_2)_6OH$ | $HOOCCH_2CH(COOH)CH_2COOH$ | 60 |
| Example 9 | $CF_3(CF_2)_7(CH_2)_{11}OH$ | $HOOCCH_2CH(COOH)CH_2COOH$ | 60 |
| Example 10 | $CF_3(CF_2)_3(CH_2)_6OH$ | $HOOCCH_2CH(COOH)CH_2COOH$ | 60 |
| Example 11 | $C_{18}H_{37}OH$ | $HOOCCH_2CH(COOH)CH_2COOH$ | 70 |

TABLE 4

| Example | Raw material compound containing Rf | Carboxylic acid raw material compound | Reaction yield (%) |
|---|---|---|---|
| Example 12 | $CF_3(CF_2)_7(CH_2)_4COCl$ | $HOCH(COOH)CH_2COOH$ | 70 |
| Example 13 | $CF_3(CF_2)_3(CH_2)_4COCl$ | $HOCH(COOH)CH_2COOH$ | 60 |
| Example 14 | $CF_3(CF_2)_3(CH_2)_7COCl$ | $HOCH(COOH)CH_2COOH$ | 60 |
| Example 15 | $CF_3(CF_2)_9(CH_2)_{10}COCl$ | $HOCH(COOH)CH_2COOH$ | 40 |
| Example 16 | $CF_3(CF_2)_7(CH_2)_{12}COCl$ | $HOCH(COOH)CH_2COOH$ | 60 |
| Example 17 | $CF_3(CF_2)_5(CH_2)_{10}COCl$ | $HOCH(COOH)CH_2COOH$ | 60 |
| Example 18 | $CF_3(CF_2)_7CH(C_9H_{19})CH_2CH=CH(CH_2)_7COCl$ | $HOCH(COOH)CH_2COOH$ | 40 |
| Example 19 | $CF_3(CF_2)_7 CH(C_6H_{13})(CH_2)_7COCl$ | $HOCH(COOH)CH_2COOH$ | 20 |
| Example 20 | $CH_3(CH_2)_3(CH_2CH_2CH(CH_2CH_2(CF_2)_9CF_3))_2(CH_2)_7COCl$ | $HOCH(COOH)CH_2COOH$ | 10 |

Next, as for the carboxylic acid type compounds of Examples 1 to 20, performance as a lubricant was tested in a manner as described below. The same test was conducted also on compounds shown in Table 5 as comparative Examples 1 to 7.

TABLE 5

| Comparative Example | Chemical formula |
|---|---|
| Comparative Example 1 | $C_{18}H_{37}NH_2$ |
| Comparative Example 2 | $CF_3(CF_2)_7(CH_2)_{10}COOCH_3$ |
| Comparative Example 3 | $C_{18}H_{37}CH(COOC_{12}H_{25})(CH_2)_2COOCH_2CF_2(OCF_2)_p(OCF(CF_3)CF_2)_qOCF_3$ (average molecular weight: 2140) |
| Comparative Example 4 | $C_{18}H_{37}CH(COOH)CH_2COOCH_2CF(CF_3)(OCF(CF_3)CF_2)_3F$ |
| Comparative Example 5 | $C_{11}H_{23}COOR_{fe}OCOC_{11}H_{23}$ ($R_{fe}$: perfluoropolyether chain having average molecular weight of 2000) |
| Comparative Example 6 | $CF_3(CF_2)_7(CH_2)_2OCO(CH_2)_3COOH$ |
| Comparative Example 7 | $C_{18}H_{37}CH(COOH)CH_2COOCH(CH_2C_6F_{13})CH_2OCOCH_2CH(COOH)C_{18}H_{37}$ |

Preparation of Sample Tape and Performance Test thereof

Cobalt was deposited on a polyethylene terephthalate film having a thickness of 6.3 μm by evaporation, to thereby form a magnetic layer comprising a metallic magnetic thin film having a thickness of 60 nm. Next, a carbon film layer having a thickness of about 10 nm was formed on the thus-formed magnetic layer by using a CVD apparatus.

Subsequently, a backcoat layer having a thickness of 0.5 μm comprising carbon and a polyurethane resin was formed on a face on the opposite side of the face on which the magnetic layer was formed of the polyethylene terephthalate film.

Thereafter, the compound as shown in Table 1, 2 or 5 was dissolved in 2-propanol and applied on a surface of the carbon film layer such that an amount of the compound to be applied became 1 mg/m² and also applied on a surface of the backcoat layer such that an amount of the compound to be applied became 3 mg/m². The resultant magnetic recording medium was cut into pieces each having a width of 8 mm, to thereby prepare sample tapes.

<Evaluation of Durability and Traveling Property>

By using thus-prepared sample tapes, friction coefficient at 40° C. and 80% RH, and shuttle durability at −5° C. or 40° C., and 20% RH were measured in such a manner as described below. The evaluation results are shown in Tables 6 and 7. Further, these conditions according to the present Example are considered to be severest among service conditions.

(1) Method for Measuring Friction Coefficient

Measurement of the friction coefficient was conducted such that a sample tape was allowed to run 1000 times on an friction coefficient measuring device placed in a thermostat, while an atmosphere therein was controlled to have a temperature of 40° C. and 80% RH. Measurements after 1000 runs thereof are shown in Tables 6 and 7 as friction coefficients.

(2) Method for Measuring Shuttle Durability

As for the shuttle durability, while an atmosphere inside a thermostat was controlled to have a temperature of −5° C. or 40° C., and 20% RH, a sample tape having a length of 230 m was allowed to run 100 times under a play mode in the thermostat and difference between an initial output and a playback output after 100 runs was measured in terms of db. At measuring the shuttle durability, a commercially available AIT2 deck (trade name: SDX-S500C; available from Sony Corporation) was used.

TABLE 6

|  | Friction coefficient (40° C., 80% RH) | Shuttle durability (dB) (−5°) | Shuttle durability (dB) (40° C., 20% RH) |
| --- | --- | --- | --- |
| Example 1 | 0.20 | −0.3 | −0.8 |
| Example 2 | 0.23 | −0.5 | −1.0 |
| Example 3 | 0.25 | −0.5 | −1.0 |
| Example 4 | 0.23 | −0.5 | −0.8 |
| Example 5 | 0.27 | −1.0 | −1.7 |
| Example 6 | 0.25 | −1.0 | −1.5 |
| Example 7 | 0.25 | −1.3 | −1.5 |
| Example 8 | 0.22 | −0.5 | −0.8 |
| Example 9 | 0.18 | −0.3 | −0.8 |
| Example 10 | 0.23 | −1.0 | −1.5 |
| Example 11 | 0.26 | −1.5 | −1.9 |
| Comparative Example 1 | 0.30 | −9.0 | −7.0 |
| Comparative Example 2 | 0.50 | −5.0 | −4.0 |
| Comparative Example 3 | 0.30 | −3.0 | −3.0 |
| Comparative Example 4 | 0.35 | −3.0 | −4.0 |

TABLE 6-continued

|  | Friction coefficient (40° C., 80% RH) | Shuttle durability (dB) (−5°) | Shuttle durability (dB) (40° C., 20% RH) |
| --- | --- | --- | --- |
| Comparative Example 5 | 0.50 | −4.0 | −3.0 |
| Comparative Example 6 | 0.55 | −3.5 | −3.5 |
| Comparative Example 7 | 0.23 | −3.5 | −4.0 |

TABLE 7

|  | Friction coefficient (40° C., 80% RH) | Shuttle durability (dB) (−5° C.) | Shuttle durability (dB) (40° C., 20% RH) |
| --- | --- | --- | --- |
| Example 12 | 0.26 | −1.0 | −1.0 |
| Example 13 | 0.27 | −1.0 | −1.3 |
| Example 14 | 0.24 | −1.2 | −1.0 |
| Example 15 | 0.20 | −0.5 | −1.0 |
| Example 16 | 0.23 | −1.0 | −1.0 |
| Example 17 | 0.23 | −0.8 | −1.0 |
| Example 18 | 0.20 | −0.5 | −1.5 |
| Example 19 | 0.24 | −1.0 | −1.5 |
| Example 20 | 0.20 | −0.5 | −1.0 |

From the results in Tables 6 and 7, as for lubricating actions of the carboxylic acid type compounds, characteristics can be pointed out as described below.

<<Change Due to Difference of Structure of Carboxylic Acid Raw Material compound having Two Carboxyl Groups>>

When a compound obtained from malic acid and a compound obtained from 1,2,3-propane tricarboxylic acid, which have a corresponding hydrophobic group (Rf) to each other, are compared with each other (for example, Example 1 and Example 9, or Example 13 or 14 and Example 10), in both of the friction coefficient and the shuttle durability, the compound of Example 9 or Example 10 which was obtained from 1,2,3-propane tricarboxylic acid is considered to have better performance than the compound of Example 1, or Example 13 or 14 which was obtained from malic acid. For example, the friction coefficients of Example 1 and Example 9 are 0.20 and 0.18, respectively and, accordingly, Example 9 is better than Example 1. Further, the friction coefficients of Examples 13 and 14 are 0.27 and 0.24, respectively, whereas the friction coefficient of Example 10 is 0.23 and, accordingly, Example 10 is slightly better than Example 13 or 14. (However, since the numbers of carbon atoms of hydrocarbon chains of Examples 13, 14 and 10 are different from one another as being 4, 7 and 6, respectively, strictly speaking, it is necessary to take these differences into consideration).

The reason why the lubricant obtained from 1,2,3-propane tricarboxylic acid has better performance than the lubricant obtained from malic acid is unknown; however, one of such reasons may be attributable to a difference in relations of positions of the two carboxyl groups and the ester bond therebetween. Regardless of the reason, the lubricant according to the invention obtained from any one of the aforementioned raw material substances is far better than Comparative Examples 1 to 6 and, compared with a difference between a conventional example, difference among Examples according to the present invention is small.

Although the lubricant in Comparative Example 7 gives a friction coefficient approximately same as the lubricant according to the present invention, the compound of Comparative Example 7 has a problem in that the shuttle durability is low.

<<Change Due to Difference of Structure of Hydrophobic Group (Rf)>>

When Examples 1 and 3, or Examples 9 and 11, in which respective carboxylic acid raw material compounds are same and numbers of entire carbon atoms of respective hydrophobic groups (Rf) are same with each other, are compared with each other, friction coefficients are 0.20 and 0.25, or 0.18 and 0.26, respectively and, accordingly, it is found that the lubricant containing a fluorine atom has a higher lubricating performance than the lubricant containing only a hydrocarbon group. Further, in a case in which malic acid derivatives which are found in a multiple of Examples are compared with one another, when Examples 2, 17, 1 and 15, in which numbers of carbon atoms of hydrocarbon chains of respective hydrophobic groups (Rf) are 10 in common with one another, are compared with one another, it is found that, as the number of carbon atoms of the fluorinated alkyl group is increased from 4 to 6 to 8 to 10 as seen in the stated order in the aforementioned Examples, the friction coefficient tends to be decreased from 0.23 to 0.23 to 0.20 to 0.20 as seen in the stated order therein. Further, when Examples 5, 12, 19, 1, 18 and 16, in which numbers of carbon atoms of respective fluorinated alkyl groups are 8 in common with one another, are compared with one another, it is found that, as the number of carbon atoms of a main chain of the hydrocarbon chain is increased from 0 to 4 to 8 to 10 to 11 to 12 as seen in the stated order in the aforementioned Examples, the friction coefficient tends to be decreased from 0.27 to 0.26 to 0.24 to 0.20 to 0.20 to 0.23 as seen in the stated order therein. From these findings, it is known that the lubricant in which the number of carbon atoms of the fluorinated alkyl group or the hydrocarbon chain is large and length of the hydrocarbon chain of the hydrophobic group (Rf) is large can realize a higher lubricating performance than other lubricants.

However, as is seen from the fact that the friction coefficient is 0.23 in Example 16 (number of carbon atoms of fluorinated alkyl group: 8; number of carbon atoms of hydrocarbon chain: 12), when the number of entire carbon atoms of the hydrophobic group (Rf) is unduly increased, the friction coefficient is increased. The reason is in that the lubricant can not evenly be applied and, then, the lubricant film is coagulated. From observations by these tests, it has been found that the friction coefficient becomes smallest in the carboxylic acid type compound in which the number of entire carbon atoms of a main chain of the hydrophobic group (Rf) is in the range of from about 16 to about 18. Further, it is found that, since a difference in the friction coefficient between Examples 4 and 7 is comparatively small, it is effective to allow length of the carbon chain of the hydrophobic group main chain which contains a fluorine atom to be large than to add a long hydrocarbon group thereto as a side chain. Also from comparisons among Examples 12 to 20, similar tendency to that as described above can be read.

<Evaluation of Corrosion Resistance>

As for the lubricants used in Examples 1 to 20 and Comparative Examples 1 to 7, storage reliability in a high-temperature, high-humidity environment and in a corrosive gas was evaluated as described below. Evaluation results are shown in Tables 8 and 9 by evaluation criteria as defined as follows:

⊙: magnetic deterioration rate is 1% or less;
○: magnetic deterioration rate is 3% or less;
Δ: magnetic deterioration rate is 5% or less; and
x: magnetic deterioration rate is more than 5%.

(1) High-temperature, High-humidity Environment

A sample in a state of a piece of tape was prepared and, then, left to stand for one week in a high-temperature, high-humidity environment of 60° C. and 80% RH and a magnetic deterioration rate between before and after such storage was measured.

(2) Corrosive Gas Environment

A sample in a state of a piece of tape was prepared and, then, left to stand for 5 hours in an environment of 35° C., 70% RH, and in an atmosphere of 2 ppm of hydrogen sulfide ($H_2S$) and 1 ppm of hydrogen chloride (HCl) and a magnetic deterioration rate between before and after such storage was measured.

TABLE 8

|  | 1<br>High-temperature, high-humidity environment | 2<br>Corrosive gas environment |
|---|---|---|
| Example 1 | ⊙ | ⊙ |
| Example 2 | ⊙ | ○ |
| Example 3 | ⊙ | ⊙ |
| Example 4 | ⊙ | ⊙ |
| Example 5 | ○ | ⊙ |
| Example 6 | ⊙ | ⊙ |
| Example 7 | ⊙ | ⊙ |
| Example 8 | ⊙ | ⊙ |
| Example 9 | ⊙ | ⊙ |
| Example 10 | ⊙ | ⊙ |
| Example 11 | ○ | ⊙ |
| Comparative Example 1 | X | Δ |
| Comparative Example 2 | X | X |
| Comparative Example 3 | X | X |
| Comparative Example 4 | X | Δ |
| Comparative Example 5 | X | X |
| Comparative Example 6 | X | Δ |
| Comparative Example 7 | ○ | ○ |

TABLE 9

|  | 1<br>High-temperature, high-humidity environment | 2<br>Corrosive gas environment |
|---|---|---|
| Example 12 | ⊙ | ⊙ |
| Example 13 | ○ | ○ |
| Example 14 | ⊙ | ○ |
| Example 15 | ⊙ | ⊙ |
| Example 16 | ⊙ | ⊙ |
| Example 17 | ⊙ | ○ |
| Example 18 | ⊙ | ⊙ |
| Example 19 | ○ | ⊙ |
| Example 20 | ○ | ⊙ |

From the results in Tables 8 and 9, it is found that all of Examples 1 to 20 based on the present invention satisfy conditions of corrosion resistance and, particularly, Examples in which the lubricant containing many fluorine atoms is used show an excellent corrosion resistance. It is considered that such feature as described above has a relation with the fact that the lubricant containing the fluorine atoms has a high water repellent property.

On the other hand, none of Comparative Examples 1 to 7 satisfies conditions of corrosion resistance at all. These results show that Comparative Example 1 in which one amino group is contained in the molecule, Comparative Example 4 in which one carboxyl group and one ester bond are contained in the molecule, and Comparative Examples 2, 3, 5 and 6 in each of, which an ester bond is contained in the molecule can not impart a magnetic recording medium with the corrosion resistance, while the carboxylic acid type compound according to the present invention containing at least two carboxyl groups and one ester bond has an advantage of being capable of imparting the magnetic recording medium with a sufficient corrosion resistance.

present invention as the lubricant for the magnetic recording medium, deterioration of the friction coefficient and shuttle durability is extremely small and an extremely favorable result on the storage durability can be obtained under various types of service conditions such as high temperature and high humidity, high temperature and low humidity, and low temperature.

In order to further perform evaluations, two groups of compounds as shown in Tables 11 and 12 were synthesized and, then, performances thereof as lubricants were compared with one another.

TABLE 11

| Example | Carboxylic acid type compound |
|---|---|
| Example 21 | $CF_3(CF_2)_3(CH_2)_2OCOCH_2CH(COOH)CH_2COOH$ |
| Example 22 | $CF_3(CF_2)_9(CH_2)_{11}OCOCH_2CH(COOH)CH_2COOH$ |
| Example 23 | $CF_3(CF_2)_3(CH_2)_{11}OCOCH_2CH(COOH)CH_2COOH$ |
| Example 24 | $CF_3(CF_2)_7(CH_2)_{13}OCOCH_2CH(COOH)CH_2COOH$ |
| Example 25 | $CF_3(CF_2)_7CH(C_9H_{19})(CH_2)_8OCOCH_2CH(COOH)CH_2COOH$ |
| Example 26 | $CF_3(CF_2)_7CH(C_6H_{13})CH_2CH=CH(CH_2)_8OCOCH_2CH(COOH)CH_2COOH$ |
| Example 27 | $CH_3(CH_2)_3(CH_2CH_2CH(CH_2CH_2(CF_2)_9CF_3))_2(CH_2)_8OCOCH_2CH(COOH)CH_2COOH$ |

TABLE 12

| Example | Carboxylic acid type compound |
|---|---|
| Example 28 | $CF_3(CF_2)_7(CH_2)_2OCOCH(C_{18}H_{37})CH_2COOCH(COOH)CH_2COOH$ |
| Example 29 | $CF_3(CF_2)_7(CH_2)_2OCOCH_2CH(C_{12}H_{25})COOCH(COOH)CH_2COOH$ |
| Example 30 | $CF_3(CF_2)_7(CH_2)_2OCOCH_2CH(C_8H_{17})COOCH(COOH)CH_2COOH$ |
| Example 31 | $CF_3(CF_2)_9(CH_2)_2OCOCH_2CH(C_{18}H_{37})COOCH(COOH)CH_2COOH$ |
| Example 32 | $CF_3(CF_2)_3(CH_2)_2OCOCH_2CH(C_{18}H_{37})COOCH(COOH)CH_2COOH$ |
| Example 33 | $CF_3(CF_2)_7(CH_2)_6OCOCH_2CH(C_{18}H_{37})COOCH(COOH)CH_2COOH$ |
| Example 34 | $CF_3(CF_2)_7(CH_2)_{11}OCOCH_2CH(C_{18}H_{37})COOCH(COOH)CH_2COOH$ |
| Example 35 | $CF_3(CF_2)_7(CH_2)_2OCOCH_2CH(C_{18}H_{35})COOCH(COOH)CH_2COOH$ |
| Example 36 | $CF_3(CF_2)_7(CH_2)_2OCOCH_2CH(CH(C_7H_{15})(C_9H_{19})COOCH(COOH)CH_2COOH$ |
| Example 37 | $CH_3(CH_2)_3(CH_2CH((CF_2)_9CF_3))_2(CH_2)_7OCOCH_2CH(C_{18}H_{37})CH(COOH)CH_2COOH$ |

<Evaluation of Solubility in Solvent>

Solubility of lubricants which were used in Examples 1 to 11 and Comparative Example 3 in each of ethanol, acetone and toluene was evaluated. Evaluation results of solubility of the lubricants are shown in Table 10 by evaluation criteria as defined as follows:

○: lubricant is easily soluble in each solvent; and x: lubricant is insoluble in solvent.

TABLE 10

| Compound | Ethanol | Acetone | Toluene |
|---|---|---|---|
| Examples 1 to 11 | ○ | ○ | ○ |
| Comparative Example 3 | X | X | X |

Comparative Example 3 selected as one of comparative examples is a lubricant which showed a comparatively favorable friction coefficient and shuttle durability among Comparative Examples. However, as shown in Table 10, since the lubricant is hardly dissolved in a hydrocarbon type solvent, it is essential to use a fluorine type solvent when the lubricant is applied and, accordingly, there is a problem in that a load to be put on the environment becomes large at the time it is used.

From the aforementioned results, it has been found that, by using the carboxylic acid type compound according to the Compounds of Examples 21 to 27 as shown in Table 11 are 1,2,3-propane tricarboxylic acid derivatives same as compounds of Examples 7 to 11 and are examples in which, mainly, numbers of carbon atoms constituting respective fluorinated alkyl groups or respective hydrocarbon chains are different from one another in various manners. An object of each of Examples 21 to 27 is to perform comparisons also of 1,2,3-propane tricarboxylic acid derivatives in a same manner as in comparisons of malic acid derivatives performed among Examples 1, 2, and 12 to 20. These compounds were synthesized by a same method as in the compound of the aforementioned Example 9.

The compounds of Examples 28 to 37 as shown in Table 12 are compounds which each have a constitution similar to that of the compound of Example 4 which has the constitution represented by the following chemical formula:

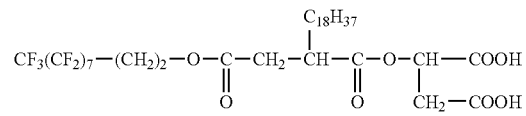

Namely, the compounds of Examples 4, and 29 to 37 each have a constitution as represented by the following general formula (7) while the compound of Example 28 has a constitution as represented by the following general formula (8):

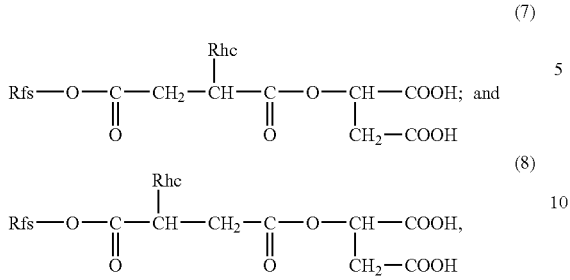

(7)

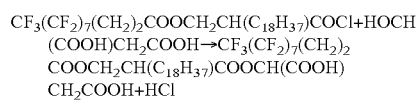

(8)

wherein Rfs represents a non-substituted or substituted, saturated or unsaturated fluorine-containing hydrocarbon group; and Rhc represents a non-substituted or substituted, saturated or unsaturated hydrocarbon group.

An object of Examples 28 to 37 is to evaluate an influence of the number of carbon atoms of a fluorinated alkyl group or a hydrocarbon chain constituting a terminal fluorine-containing hydrocarbon group Rfs or an influence of the number of carbon atoms of a hydrocarbon group Rhc by comparisons in a same manner as has been performed in Examples 1, 2, and 12 to 20.

The compounds of Examples 28 to 37 were synthesized by a same synthesis method as that in the compound of Example 4 to be described below. The synthesis method is same as that in the compound of Example 1 except that toluene was used in place of THF as a solvent for forming a reaction mixture.

Synthesis of Compound of Example 4

A fluorine-containing carboxylic acid chloride: $CF_3(CF_2)_7(CH_2)_2COOCH_2CH(C_{18}H_{37})COCl$ as an acid chloride compound containing an Rf group in the general formula (2) and malic acid as a compound containing a carboxyl group in the general formula (2) were allowed to react with each other in accordance with the following reaction formula to synthesize the compound of Example 4 which is a carboxylic acid type compound according to the present invention in the stated order in synthesis procedures as described below:

$CF_3(CF_2)_7(CH_2)_2COOCH_2CH(C_{18}H_{37})COCl+HOCH$
$(COOH)CH_2COOH \rightarrow CF_3(CF_2)_7(CH_2)_2$
$COOCH_2CH(C_{18}H_{37})COOCH(COOH)$
$CH_2COOH+HCl$ 42.8 g of $CF_3(CF_2)_7(CH_2)_2COOCH_2CH(C_{18}H_{37})COCl$ and 6.7 g of malic acid were mixed in 500 ml of toluene and heated for 3 hours in a reflux manner to allow them to react with each other. After such reaction was terminated, toluene was filtered out and, then, a resultant reaction product was purified by recrystallization. Namely, a reaction liquid was filtered to separate the reaction product in a solid state from toluene and, then, after the reaction product was dissolved in 500 ml of 2-propanol (IPA) heated at 60° C., an impurity was removed by filtration to collect a filtrate which was, subsequently, condensed and, then, after the thus-condensed filtrate was dissolved in 500 ml of n-hexane heated at 60° C., the resultant mixture was cooled by ice to allow a subject article to be precipitated as a crystal. The crystal was collected by filtration and, accordingly, the purified subject article was obtained. A yield thereof was about 60%.

Figure 8:
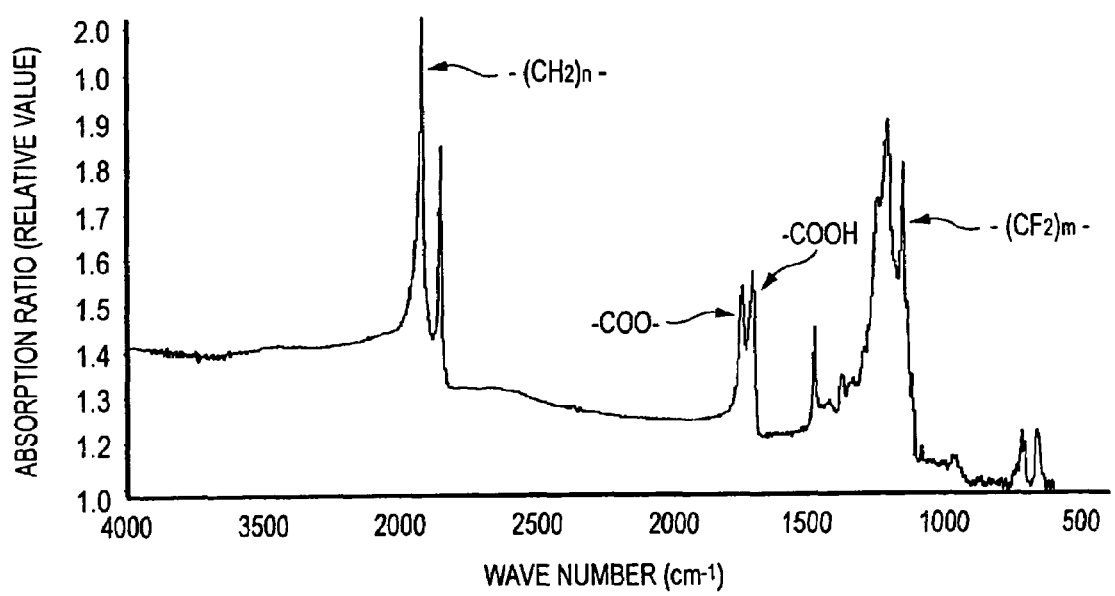
FIG. 8 is a graph showing an infrared light absorption spectrum of a carboxylic acid type compound of Example 4 according to the present invention.

When a product, namely, the subject article, was measured by using an infrared absorption spectrum (IR) method and a liquid chromatography mass spectrometry (LCMS), respective results thereof were obtained as shown in FIGS. 8 and 9. From these results, the product was found to be a compound as expressed by the chemical formula: $CF_3(CF_2)_7(CH_2)_2COOCH_2CH(C_{18}H_{37})COOCH(COOH)CH_2COOH$ (molecular weight: 932.8). Further, a peak found between 973 and 974 is that of an associated body of the compound and the solvent and is often detected by the LCMS.

Reaction substances used in synthesis of compounds of Examples 21 to 27, and Examples 28 to 37, and reaction yields are shown in Tables 13 and 14.

TABLE 13

| Example | Raw material compound containing Rf | Carboxylic acid raw material compound | Reaction ratio |
|---|---|---|---|
| Example 21 | $CF_3(CF_2)_3(CH_2)_2OH$ | $HOOCCH_2CH(COOH)CH_2COOH$ | 60 |
| Example 22 | $CF_3(CF_2)_9(CH_2)_{11}OH$ | $HOOCCH_2CH(COOH)CH_2COOH$ | 60 |
| Example 23 | $CF_3(CF_2)_3(CH_2)_{11}OH$ | $HOOCCH_2CH(COOH)CH_2COOH$ | 60 |
| Example 24 | $CF_3(CF_2)_7(CH_2)_{13}OH$ | $HOOCCH_2CH(COOH)CH_2COOH$ | 40 |
| Example 25 | $CF_3(CF_2)_7CH(C_9H_{19})(CH_2)_8OH$ | $HOOCCH_2CH(COOH)CH_2COOH$ | 30 |
| Example 26 | $CF_3(CF_2)_7CH(C_6H_{13})CH_2CH=CH(CH_2)_8OH$ | $HOOCCH_2CH(COOH)CH_2COOH$ | 10 |
| Example 27 | $CH_3(CH_2)_3(CH_2CH_2CH(CH_2CH_2(CF_2)_9CF_3))_2CH_2)_8OH$ | $HOOCCH_2CH(COOH)CH_2COOH$ | 10 |

TABLE 14

| Example | Raw material compound containing Rf | Carboxylic acid raw material compound | Reaction ratio (%) |
|---|---|---|---|
| Example 28 | $CF_3(CF_2)_7(CH_2)_2OCOCH(C_{18}H_{37})CH_2COCl$ | $HOCH_2CH(COOH)CH_2COOH$ | 60 |
| Example 29 | $CF_3(CF_2)_7(CH_2)_2OCOCH_2CH(C_{12}H_{25})COCl$ | $HOCH_2CH(COOH)CH_2COOH$ | 60 |

TABLE 14-continued

| Example | Raw material compound containing Rf | Carboxylic acid raw material compound | Reaction ratio (%) |
|---|---|---|---|
| Example 30 | $CF_3(CF_2)_7(CH_2)_2OCOCH_2CH(C_8H_{17})COCl$ | $HOCH_2CH(COOH)CH_2COOH$ | 60 |
| Example 31 | $CF_3(CF_2)_9(CH_2)_2OCOCH_2CH(C_{18}H_{37})COCl$ | $HOCH_2CH(COOH)CH_2COOH$ | 60 |
| Example 32 | $CF_3(CF_2)_3(CH_2)_2OCOCH_2CH(C_{18}H_{37})COCl$ | $HOCH_2CH(COOH)CH_2COOH$ | 60 |
| Example 33 | $CF_3(CF_2)_7(CH_2)_6OCOCH_2CH(C_{18}H_{37})COCl$ | $HOCH_2CH(COOH)CH_2COOH$ | 60 |
| Example 34 | $CF_3(CF_2)_7(CH_2)_{11}OCOCH_2CH(C_{18}H_{37})COCl$ | $HOCH_2CH(COOH)CH_2COOH$ | 50 |
| Example 35 | $CF_3(CF_2)_7(CH_2)_2OCOCH_2CH(C_{18}H_{35})COCl$ | $HOCH_2CH(COOH)CH_2COOH$ | 60 |
| Example 36 | $CF_3(CF_2)_7(CH_2)_2OCOCH_2CH(CH(C_7H_{15})(C_9H_{19})COCl$ | $HOCH_2CH(COOH)CH_2COOH$ | 60 |
| Example 37 | $CH_3(CH_2)_3(CH_2CH(CF_2)_9CF_3))_2(CH_2)_7OCOCH_2CH(C_{18}H_{37})COCl$ | $HOCH_2CH(COOH)CH_2COOH)$ | 10 |

Next, sample tapes of carboxylic acid type compounds of Example 21 to 37 were prepared in a same manner as in Examples 1 to 20 and, using thus-prepared sample tapes, friction coefficient and shuttle durability of each Example were measured for evaluating a traveling property and durability. The results are shown in Tables 15 and 16.

TABLE 15

| | Friction coefficient (40° C., 80% RH) | Shuttle durability (dB) (−5° C.) | Shuttle durability (dB) (40° C., 20% RH) |
|---|---|---|---|
| Example 21 | 0.28 | −1.5 | −2.0 |
| Example 22 | 0.20 | −0.5 | −1.0 |
| Example 23 | 0.20 | −1.0 | −1.5 |
| Example 24 | 0.20 | −0.5 | −0.8 |
| Example 25 | 0.20 | −0.5 | −1.0 |
| Example 26 | 0.25 | −1.0 | −1.0 |
| Example 27 | 0.23 | −0.5 | −1.0 |

TABLE 16

| | Friction coefficient (40° C., 80% RH) | Shuttle durability (dB) (−5° C.) | Shuttle durability (dB) (40° C., 20% RH) |
|---|---|---|---|
| Example 28 | 0.23 | −0.5 | −0.8 |
| Example 29 | 0.25 | −0.8 | −1.0 |
| Example 30 | 0.27 | −1.0 | −1.5 |
| Example 31 | 0.22 | −1.0 | −0.8 |
| Example 32 | 0.25 | −0.5 | −1.0 |
| Example 33 | 0.22 | −0.5 | −1.0 |
| Example 34 | 0.20 | −0.5 | −0.8 |
| Example 35 | 0.24 | −1.0 | −1.0 |
| Example 36 | 0.23 | −1.0 | −1.0 |
| Example 37 | 0.21 | −1.0 | −1.0 |

From results in Tables 15 and 16, as for lubricating actions of the carboxylic acid type compounds, same characteristics as described above can be pointed out.

In a case in which 1,2,3-propane tricarboxylic acid derivatives obtained in a multiple of Examples are compared with one another, when Examples 23, 9 and 22, in which numbers of carbon atoms of hydrocarbon chains constituting respective hydrophobic groups (Rf) are 11 in common with one another, are compared with one another, it is found that, as the number of carbon atoms of the fluorinated alkyl group is increased from 4 to 8 to 10 as seen in the stated order in the aforementioned Examples, the friction coefficient tends to be decreased from 0.20 to 0.18 to 0.20 as seen in the stated order therein. Further, when Examples 7, 8, 25, 9 and 24, in which numbers of carbon atoms of respective fluorinated alkyl groups are 8 in common with one another, are compared with one another, it is found that, as the number of carbon atoms of the hydrocarbon chain is increased from 2 to 6 to 8 to 11 to 13 as seen in the stated order in the aforementioned Examples, the friction coefficient tends to be decreased from 0.25 to 0.22 to 0.20 to 0.18 to 0.20 as seen in the stated order therein. From these findings, it is known that the lubricant in which the number of carbon atoms of the fluorinated alkyl group or the main chain of the hydrocarbon chain is large and length of the hydrocarbon chain of a main chain of the hydrophobic group (Rf) is large can realize a higher lubricating performance than other lubricants. However, as is seen from the fact that the friction coefficient is 0.20 in Example 22 (number of carbon atoms of fluorinated alkyl group: 10; number of carbon atoms of hydrocarbon chain: 11) and Example 24 (number of carbon atoms of fluorinated alkyl group: 8; number of carbon atoms of hydrocarbon chain: 13), when the number of entire carbon atoms of the hydrophobic group (Rf) is unduly increased, the friction coefficient is increased. The reason is in that the lubricant can not evenly be applied and, then, the lubricant film is coagulated. From observations of these tests, it has been found that the friction coefficient becomes smallest in the carboxylic acid type compound in which the number of entire carbon atoms of the main chain of the hydrophobic group (Rf) is in the range of from about 16 to about 18. As has been described above, it has been found that, a tendency found in Examples 1 to 20 can also be observed in Examples 21 to 27.

As shown in Table 16, it has been found that there is a same tendency as described above also in Examples 28 to 37 which are carboxylic acid type compounds each having a constitution common to that of Example 4. Further, when Examples 30, 29 and 4 which have a same constitution except for a hydrocarbon group Rhc were compared with one another, it has been found that, as the hydrocarbon group Rhc became larger from $—C_8H_{17}$ to $—C_{12}H_{25}$ to $C_{18}H_{37}$, the friction coefficient was decreased from 0.27 to 0.25 to 0.23 and, accordingly, the hydrocarbon group Rhc contributed to reduction of the friction coefficient. However, in a same manner as described above, an effect to be obtained by allowing length of the hydrocarbon chain of such side chain to be large is smaller than that obtained by allowing length of the hydrocarbon chain of the hydrophobic group to be large.

<Evaluation of Corrosion Resistance>

As for the lubricants used in Examples 21 to 37, storage reliability against a high-temperature, high-humidity environment and a corrosive gas was evaluated in a same manner as in Examples 1 to 20. Evaluation results are shown in Tables 17 and 18 by evaluation criteria of (1) high-temperature and high-humidity environment and (2) corrosive gas environment as defined as follows:

⊙: magnetic deterioration rate is 1% or less;
○: magnetic deterioration rate is 3% or less;
Δ: magnetic deterioration rate is 5% or less; and
x: magnetic deterioration rate is more than 5%.

TABLE 17

| Example | 1<br>High-temperature,<br>high-humidity environment | 2<br>Corrosive gas environment |
|---|---|---|
| Example 21 | ○ | ○ |
| Example 22 | ⊙ | ⊙ |
| Example 23 | ⊙ | ○ |
| Example 24 | ⊙ | ⊙ |
| Example 25 | ⊙ | ⊙ |
| Example 26 | ○ | ⊙ |
| Example 27 | ○ | ⊙ |

TABLE 18

| Example | 1<br>High-temperature,<br>high-humidity environment | 2<br>Corrosive gas environment |
|---|---|---|
| Example 28 | ⊙ | ⊙ |
| Example 29 | ⊙ | ⊙ |
| Example 30 | ○ | ⊙ |
| Example 31 | ⊙ | ⊙ |
| Example 32 | ○ | ⊙ |
| Example 33 | ⊙ | ⊙ |
| Example 34 | ⊙ | ⊙ |
| Example 35 | ⊙ | ⊙ |
| Example 36 | ○ | ⊙ |
| Example 37 | ⊙ | ⊙ |

From results in Tables 17 and 18, all of Examples 21 to 37 based on the present invention satisfy conditions of corrosion resistance. As described above, it is found that, particularly, Examples in which the lubricant containing many fluorine atoms is used show an excellent corrosion resistance. It is considered that such feature as described above has a relation with the fact that the lubricant containing the fluorine atoms has a high water repellent property.

<Evaluation of Solubility in Solvent>

Solubility of lubricants which were used in Examples 21 to 37 in each of ethanol, acetone and toluene was evaluated. Evaluation results of solubility of lubricants are shown in Table 19 by evaluation criteria as defined as follows:

○: lubricant is easily soluble in each solvent; and
x: lubricant is insoluble in solvent.

TABLE 19

| Compound | Ethanol | Acetone | Toluene |
|---|---|---|---|
| Examples 21 to 37 | ○ | ○ | ○ |

While the present invention has been described above with reference to illustrative embodiments and examples, it should be noted that the invention is by no means limited thereto, and various improvements and modifications may of course be made without departing from the scope and spirit of the invention.

The carboxylic acid type compound according to the present invention is advantageous as a lubricant, particularly, for a magnetic recording medium. Further, when the carboxylic acid type compound according to the present invention is used as the lubricant for a recording medium, the recording medium in which an excellent lubricating property is held in various types of service conditions and a lubricating effect can be maintained for a long period of time and which can provide an excellent traveling property, abrasion resistance, durability, storability and the like can be obtained.

What is claimed is:

1. A recording medium, containing on a recording layer, in the recording layer, or on and in the recording layer a lubricant comprising a carboxylic acid compound having at least two carboxyl groups and one ester bond as represented by the following general formula (1):

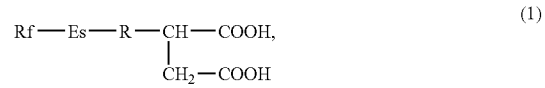

wherein Rf represents a non-substituted or substituted, saturated or unsaturated fluorine-containing hydrocarbon group or hydrocarbon group;

Es represents an ester bond; and

R may be omitted or represent a non-substituted or substituted, saturated or unsaturated hydrocarbon group.

2. The recording medium as set forth in claim 1, wherein the lubricant comprises a carboxylic acid compound as represented by the following general formula (2):

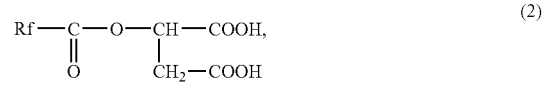

wherein Rf represents a non-substituted or substituted, saturated or unsaturated fluorine-containing hydrocarbon group or hydrocarbon group.

3. The recording medium as set forth in claim 1, wherein the lubricant comprises a carboxylic acid compound as represented by the following general formula (3):

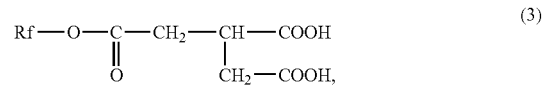

wherein Rf represents a non-substituted or substituted, saturated or unsaturated fluorine-containing hydrocarbon group or hydrocarbon group.

4. The recording medium as set forth in claim 2 or 3, wherein Rf represents a saturated or unsaturated fluorine-containing hydrocarbon having from 6 to 50 carbon atoms in total and from 4 to 20 carbon atoms in a fluorinated hydrocarbon group.

5. The recording medium as set forth in any one of claims 1 to 4, being constituted as a magnetic recording medium in which the recording layer is a magnetic layer.

6. A recording medium, containing, either incorporated within or on a layer above a recording layer, or in or above the recording layer, or above and in the recording layer a lubricant comprising a carboxylic acid compound having at least two carboxyl groups and one ester bond as represented by the following general formula (1):

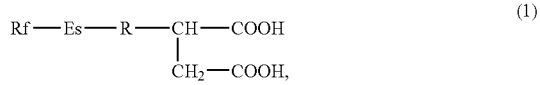
(1)

wherein Rf represents a non-substituted or substituted, saturated or unsaturated fluorine-containing hydrocarbon group or hydrocarbon group;

Es represents an ester bond; and

R may be omitted or represent a non-substituted or substituted, saturated or unsaturated hydrocarbon group.

7. The recording medium as set forth in claim 6, wherein the lubricant comprises a carboxylic acid compound as represented by the following general formula (2):

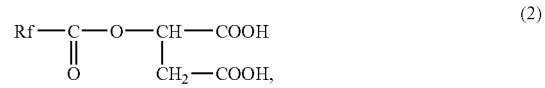
(2)

wherein Rf represents a non-substituted or substituted, saturated or unsaturated fluorine-containing hydrocarbon group or hydrocarbon group.

8. The recording medium as set forth in claim 6, wherein the lubricant comprises a carboxylic acid compound as represented by the following general formula (3):

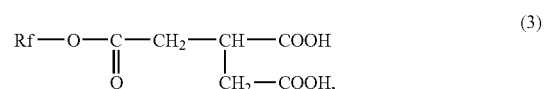
(3)

wherein Rf represents a non-substituted or substituted, saturated or unsaturated fluorine-containing hydrocarbon group or hydrocarbon group.

9. The recording medium as set forth in claim 7 or 8, wherein Rf represents a saturated or unsaturated fluorine-containing hydrocarbon having from 6 to 50 carbon atoms in total and from 4 to 20 carbon atoms in a fluorinated hydrocarbon group.

10. The recording medium as set forth in any one of claims 6 to 9, being constituted as a magnetic recording medium in which the recording layer is a magnetic layer.

* * * * *